United States Patent [19]
Sato et al.

[11] Patent Number: 5,526,089
[45] Date of Patent: Jun. 11, 1996

[54] CAMERA WITH SIGHT LINE DETECTING DEVICE

[75] Inventors: Shigemasa Sato, Yokohama; Toshimi Watanabe, Machida, both of Japan

[73] Assignee: Nikon Corporation, Tokyo, Japan

[21] Appl. No.: 436,599

[22] Filed: May 8, 1995

Related U.S. Application Data

[63] Continuation of Ser. No. 118,330, Sep. 9, 1993, abandoned.

[30] Foreign Application Priority Data

Sep. 14, 1992 [JP] Japan ..................... 4-245195
Aug. 12, 1993 [JP] Japan ..................... 5-200544

[51] Int. Cl.⁶ ............................. G03B 7/00; G03B 29/00
[52] U.S. Cl. ............................. 354/410; 354/62; 354/219
[58] Field of Search ............................. 354/400, 402, 354/410, 62, 219, 266; 351/211

[56] References Cited

U.S. PATENT DOCUMENTS

| | | | |
|---|---|---|---|
| 5,036,347 | 7/1991 | Tsunekawa et al. | 354/62 |
| 5,182,443 | 1/1993 | Suda et al. | 250/201.2 |
| 5,239,337 | 8/1993 | Takagi et al. | 354/219 |
| 5,280,312 | 1/1994 | Yamada et al. | 351/211 |
| 5,291,234 | 3/1994 | Shindo et al. | 354/402 |
| 5,298,927 | 3/1994 | Konishi et al. | 351/211 |
| 5,386,258 | 1/1995 | Magano | 354/400 |

FOREIGN PATENT DOCUMENTS

| | | |
|---|---|---|
| 0499320 | 8/1992 | European Pat. Off. |
| 2824790 | 12/1978 | Germany. |
| 2-5 | 1/1990 | Japan. |
| 2-138673 | 5/1990 | Japan. |
| 2-264633 | 10/1990 | Japan. |
| 4-28336 | 1/1992 | Japan. |
| 4-138431 | 5/1992 | Japan. |
| WO81/02084 | 7/1981 | WIPO. |
| WO89/02585 | 3/1989 | WIPO. |

*Primary Examiner*—Russell E. Adams
*Attorney, Agent, or Firm*—Shapiro and Shapiro

[57] ABSTRACT

A camera having a sight line detecting device is provided with an illumination unit for detecting the corneal reflected image of the eye of the photographer, and an illumination unit equipped with plural light sources positioned around an eyepiece lens, for detecting the position of the center of the pupil. The latter illumination unit, for detecting the position of the center of the pupil, is so controlled that a light source positioned below or at the side of the eye of the photographer is turned on regardless of the change in the camera attitude, whereby the illuminating light is not intercepted by the eyelid or eyelashes and the position of the pupil center can be precisely detected.

17 Claims, 20 Drawing Sheets

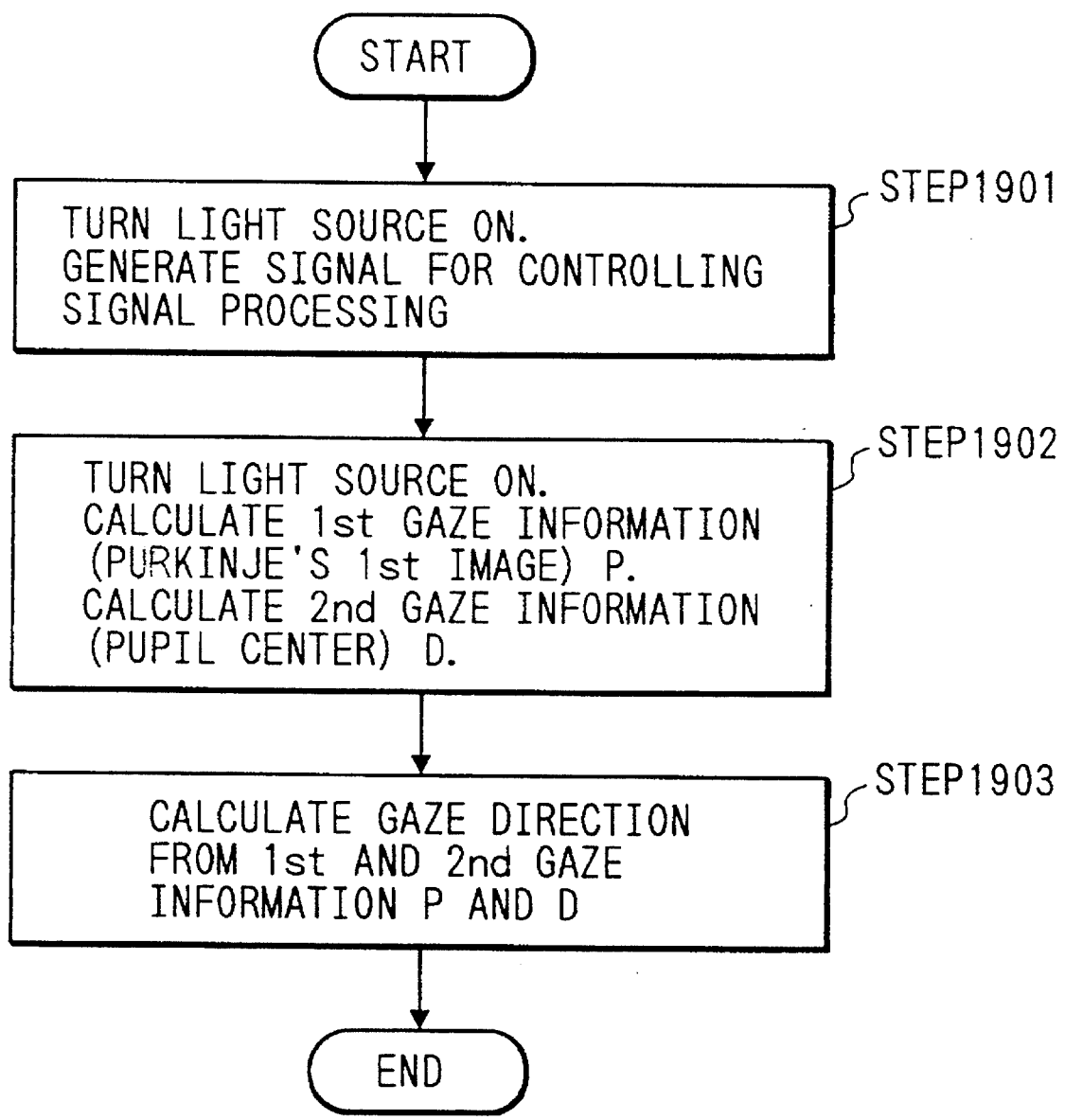

FIG. 32 PRIOR ART
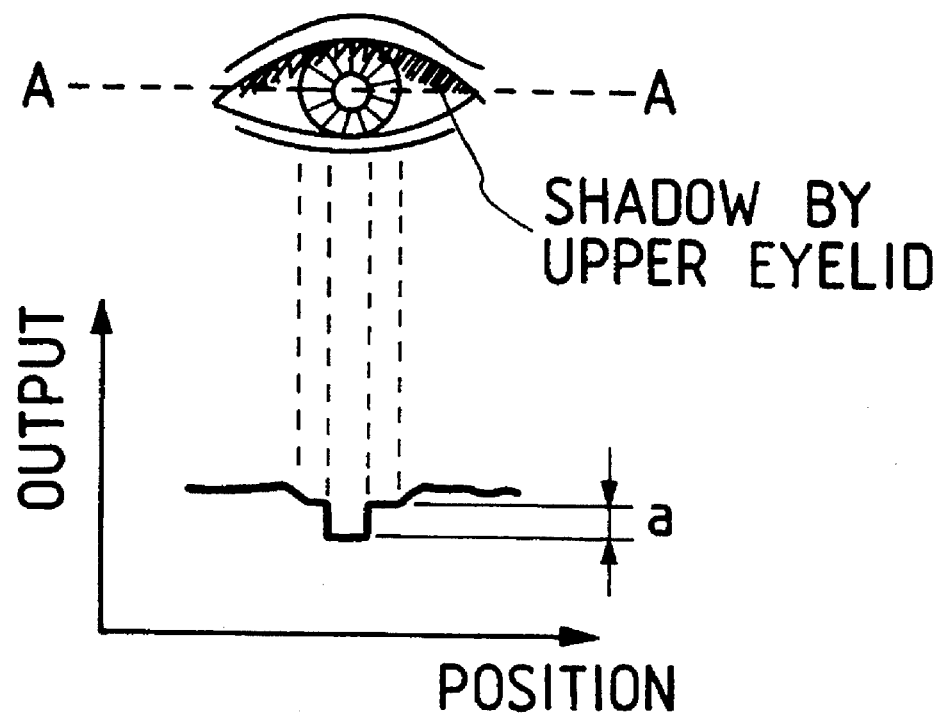
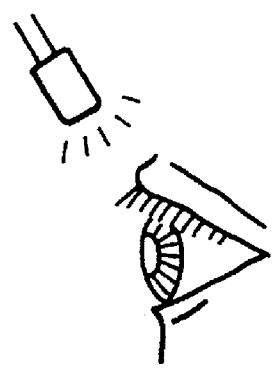

CAMERA WITH SIGHT LINE DETECTING DEVICE

This is a continuation of application Ser. No. 08/118,330 filed Sep. 9, 1993, now abandoned.

BACKGROUND OF THE INVENTION

1. Field of the Invention

The present invention relates to a camera provided with a sight line detecting device capable of detecting the line of sight of the photographer and thereby detecting the object to be photographed.

2. Related Background Art

For detecting the line of sight of the photographer, there is already known a method, as disclosed in the Japanese Patent Laid-Open Application No. 2-5, of illuminating the eye of the photographer and detecting the position of the line of sight thereof from the relative position of the reflected image of the illuminating light on the cornea (hereinafter called Purkinje's first image) and the center of the pupil. Also there is known, as disclosed in the Japanese Patent Laid-Open Application No. 2-138673, a method of illuminating the eye with light sources positioned around an optical system for eye observation, in order to facilitate the detection of the boundary between the pupil and the iris.

Though the Purkinje's first image is detectable with a light source of a relatively low illuminating intensity, the detection of the boundary of the pupil and the iris requires illumination with a light source of considerably high illuminating intensity. It has therefore been difficult to efficiently detect both the Purkinje's first image and the boundary between the pupil and the iris by a same light source, particularly a light source providing a substantially parallel light beam formed by an optical system. Also a configuration with light sources positioned around the optical system for observing the eye may form a shadow of the upper eyelid or the eyelashes depending on the position of the light sources, or a shadow depending on the relative position of the observing optical system and the eye, as will be explained in the following with reference to FIG. 32. FIG. 32 indicates the output of a photoelectric converting element in the ordinate and the position of said element in the abscissa, and showing shows an example of the output signal in a detection line A in case the eye is illuminated by a light source positioned at the upper side of the eye. In this example, the shadow of the upper eyelid is formed in the white and the black of the eye, as well as in the pupil, and a signal resulting from said shadow is superposed on the signal of the eye image. For this reason the difference a between the outputs corresponding to the pupil and the iris becomes smaller, and the precise calculation of the center of the pupil becomes difficult.

SUMMARY OF THE INVENTION

The camera provided with the sight line detecting device of the present invention is provided with an illumination unit for detecting the corneal reflected image of the eye of the photographer, and an illumination unit equipped with plural light sources positioned around an eyepiece lens, for detecting the position of the center of the pupil. The latter illumination unit, for detecting the position of the center of the pupil, is so controlled that a light source positioned below or at the side of the eye of the photographer is turned on regardless of the change in the camera attitude, whereby the illuminating light is not intercepted by the eyelid or eyelashes and the position of the pupil center can be precisely detected.

Also the output of the photoelectric converting element, receiving the eye image of the photographer, can be processed from the lower side or in an arbitrary manner, so that the unnecessary signal portion in said element need not be processed and the time required for sight line detection can be shortened.

BRIEF DESCRIPTION OF THE DRAWINGS

FIG. 11 is a view showing an example of the output of the photoelectric converting element 117 when the first illumination unit 10 is turned on;

FIG. 12 is a view showing an example of the output of the photoelectric converting element 117 when the second illumination unit 11 is turned on;

FIG. 19 is a flow chart showing a sight line detecting subroutine in FIG. 7;

FIG. 32 is a view showing an example of the output of the photoelectric converting element in a conventional camera with a sight line detecting device.

DETAILED DESCRIPTION OF THE PREFERRED EMBODIMENTS

Now the present invention will be clarified described in detail with respect to preferred embodiments thereof.

First Embodiment

Figure 1:
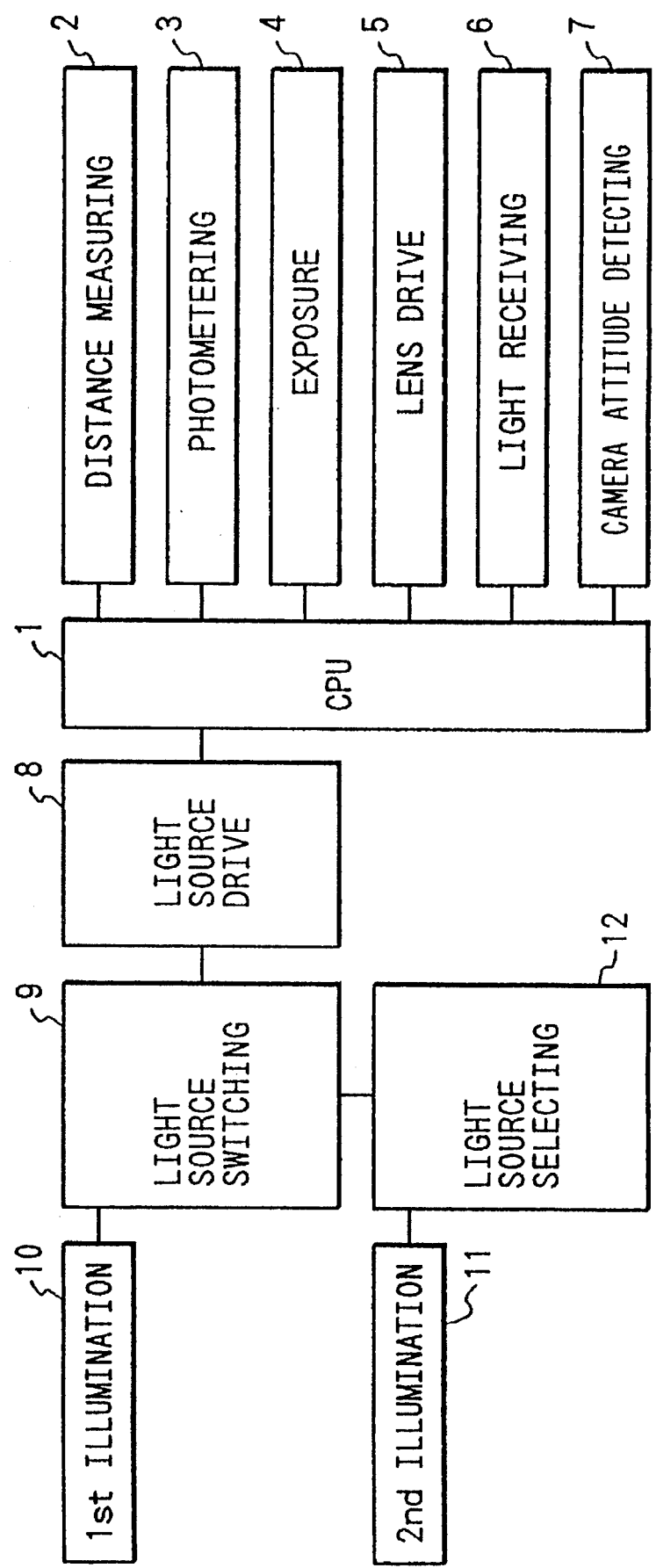
FIG. 1 is a block diagram of a camera with a sight line detecting device, constituting a first embodiment of the present invention.
Figure 2:
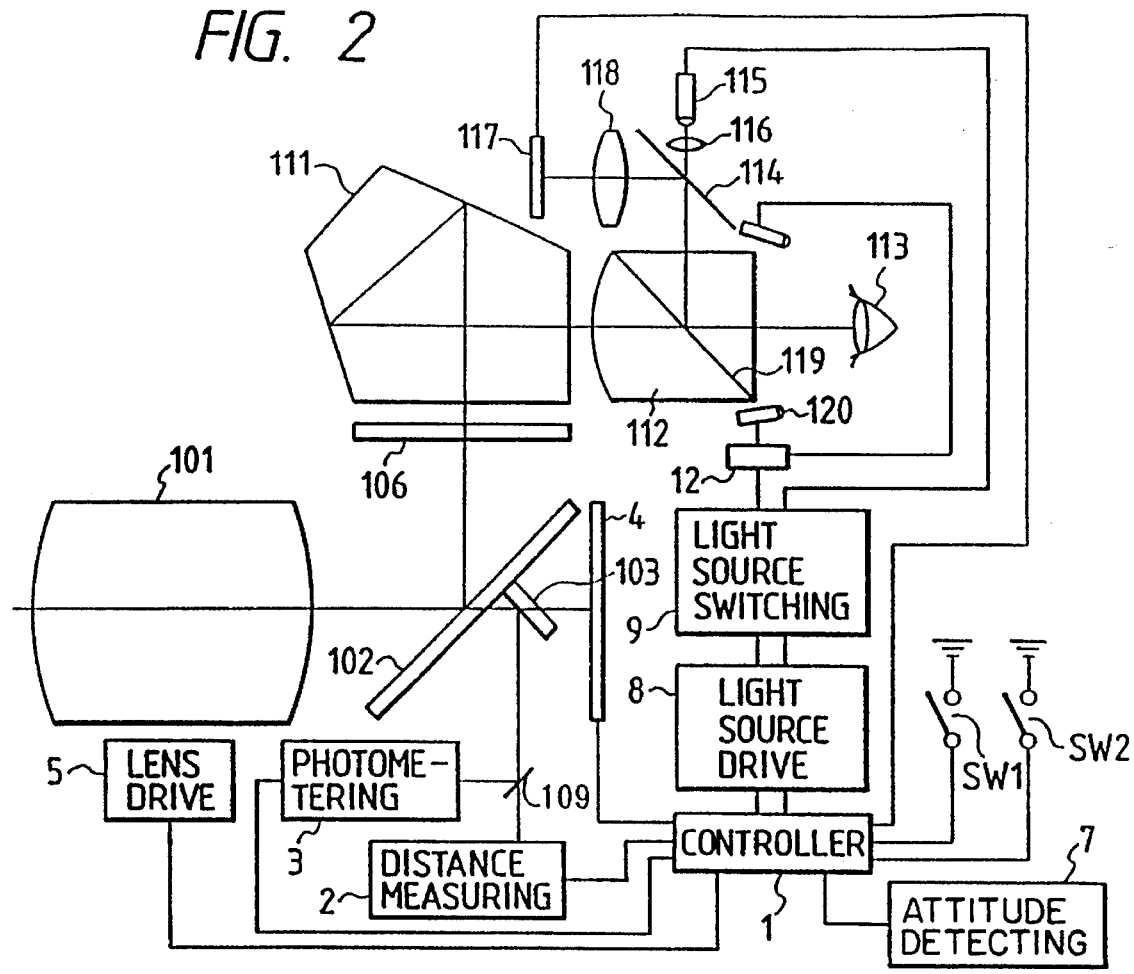
FIG. 2 is a schematic view of the camera with the sight line detecting device of said first embodiment.

FIG. 1 is a block diagram showing a first embodiment of the camera with the sight line detecting device of the present invention, and FIG. 2 is a schematic view, including an optical system, of said camera of the first embodiment.

Referring to FIGS. 1 and 2, a control unit 1 is composed of a CPU effecting the control of the entire camera, with the sight line detecting device, of the first embodiment.

Figure 8:
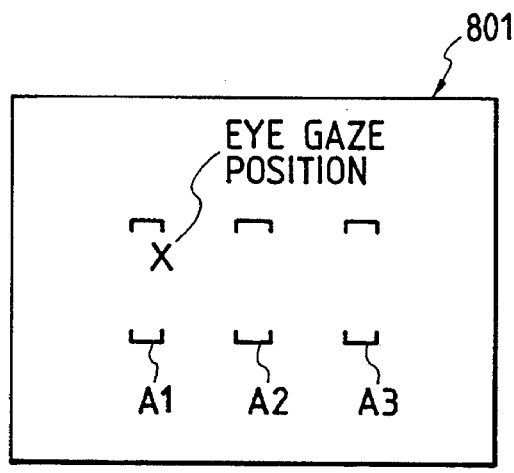
FIG. 8 is a view showing an AF area in the view finder of the camera with the sight line detecting device of the first embodiment.

A distance measuring unit 2 can effect distance measurement in each of plural distance measuring areas A1, A2, A3 formed, as shown in FIG. 8, in a view finder 801. Though discrete areas are provided in this embodiment, there may be provided continuous areas.

A photometry unit 3 can effect light metering in each of plural areas divided in the phototaking field (viewing field of the view finder).

An exposure unit 4 effects the exposure operation, based on an exposure value calculated by the control unit 1.

A lens driving unit 5 drives a phototaking lens 101, corresponding to the moving amount of a focusing lens, calculated by the control unit 1.

A light-receiving unit 6 is composed of an optical system 118 and a photoelectric converting element 117 shown in FIG. 2. The photoelectric converting element 117 is composed, for example of a one- or two-dimensional CCD. The signal from said element 117 is supplied to the control unit 1 for detecting the positions of the Purkinje's first image and of the pupil center, according to which the direction of the line of sight is calculated by the control unit 1.

An attitude detecting unit 7 detects whether the camera is held in a horizontal or vertical attitude.

A light source driving unit 8 serves to drive the light sources for sight line detection, and said light sources are turned on or off by the control unit 1.

A light source switching unit 9 switches a first illumination unit 10 and a second illumination unit 11, under the control of the control unit 1.

A first illumination unit 10, for detecting the Purkinje's first image, is composed of a light source 115 and an optical system 116, as shown in FIG. 2. The light from the light source 115 is guided through the optical system 116, then reflected by a light path splitter 119 in an eyepiece lens 112 and illuminates the eye of the photographer, as a substantially parallel light beam.

Said light source 115, for detecting the Purkinje's first image, is connected to and controlled by the control unit 1. The light source 115 is composed of an infrared light-emitting diode (LED), and the emitted light is guided through the optical system 116, then deflected toward the eye 113 of the photographer by a half mirror 119 in the eyepiece lens 112, and illuminates the eye 113 as a substantially parallel light beam. Said half mirror 119 is composed of a dichroic mirror reflecting the infrared light.

The light from the light source 115, reflected by the eye 113, is deflected toward the light source 115 by the half mirror 119 in the eyepiece lens 112, then further deflected by a half mirror 114 for separating the light from the light source 115 and the reflected light from and the eye, and reaches the photoelectric converting element 117 through an optical system 118. Thus, on the photoelectric converting element 117, there is focused the reflected image by the cornea of the eye 113 of the photographer, namely the Purkinje's first image. Said element 117 is connected to the control unit 1, so that the output signal of said element 117 is supplied to the control unit 1.

The second illumination unit 11, for detecting the position of the pupil center, is provided with plural light sources 120 positioned around the eyepiece lens 112. Said second illumination unit 11 directly illuminates the eye 113 of the photographer, without employing the optical system as in the first illumination unit 10.

Said light sources 120 are composed of plural infrared LED's positioned around the eyepiece lens 112, for detecting the boundary between the pupil and the iris, or obtaining the image of the eye 113. Said light sources are also connected to and controlled by the control unit 1.

The light from said light sources 120, reflected by the eye 113, is deflected toward the light source 115 by the half mirror 119 in the eyepiece lens 112, then further deflected by the half mirror for separating the light from the light source 115 and the reflected light from the eye 113, and reaches the photoelectric converting element 117 through the optical system 118. Thus, on said element 117 there is focused the image of the eye 113 of the photographer, and the image signal of said eye is also supplied to the control unit 1. The arrangement of the light sources 120 will be explained later in more detail.

A half-stroke switch SW1 is connected to the control unit 1, and is turned on by a half-stroke depression of a shutter release button.

A full-stroke switch SW2, also connected to the control unit 1, is turned on by a full-stroke depression of the shutter release button.

A light source selecting unit 12 selects the light sources to be used, among the plural light sources 120 of the second illumination unit 11, positioned around the eyepiece lens 112 for the purpose of detecting the position of the pupil center, and is controlled by a signal from the attitude detecting unit 7.

Now referring to FIG. 2, the light coming from an object and transmitted by a phototaking lens 101 is split by a main mirror 102 to the light proceeding to a finder screen 106 and the light proceeding to the distance measuring unit 2 and the photometry unit 3, and the latter is further deflected by a sub mirror 103 toward the distance measuring unit 2. A part of the light proceeding to said distance measuring unit 2 is split by a half mirror 109 and is guided to the photometry unit 3. On the other hand, the light split by the main mirror 102 toward the finder screen 106, is used to form a focused image of the object on said screen 106, and said object image is guided through a view finder 111 to-the eye 113 of the photographer.

Figure 3:
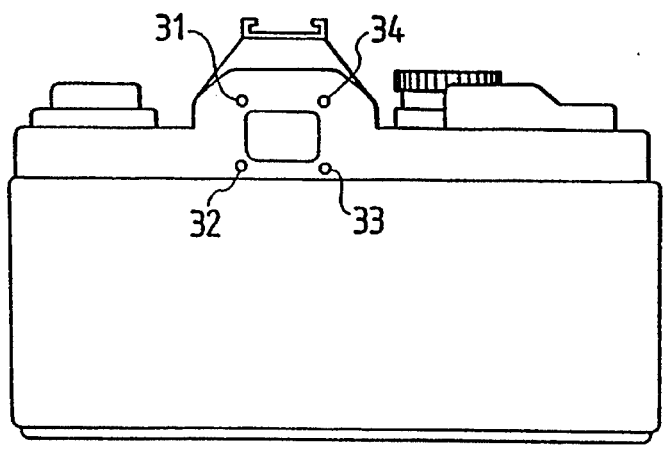
FIG. 3 is a view showing the arrangement of light sources in a second illumination unit, for use in the camera with the sight line detecting device of said first embodiment.

FIG. 3 illustrates an example of the arrangement of the light sources 120 of the second illumination unit, illuminating the eye 113 of the photographer for detecting the position of the pupil center.

As shown in FIG. 3, there are provided four light sources in total composed of infrared LED's 31–34 in this embodiment (hereinafter simply called LED's), respectively in the vicinity of the diagonal corners of the eyepiece lens. Said four LED's are selectively used, by the light source selecting unit 12, according to the output of the attitude detecting unit 7 for detecting the camera position. In this embodiment, the two LED's positioned lower in the direction of gravity are used, according to the output of said attitude detecting unit 7.

Figure 4A:
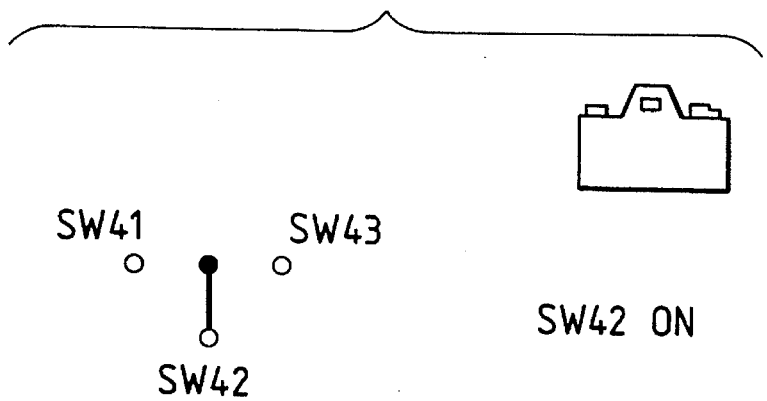
FIGS. 4A, 4B and 4C are views showing the functions of a position detecting unit 7.
Figure 4B:
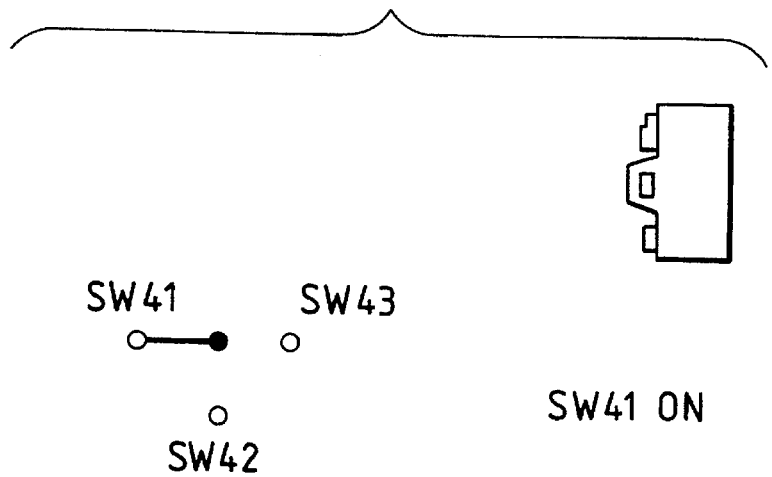
Figure 4C:
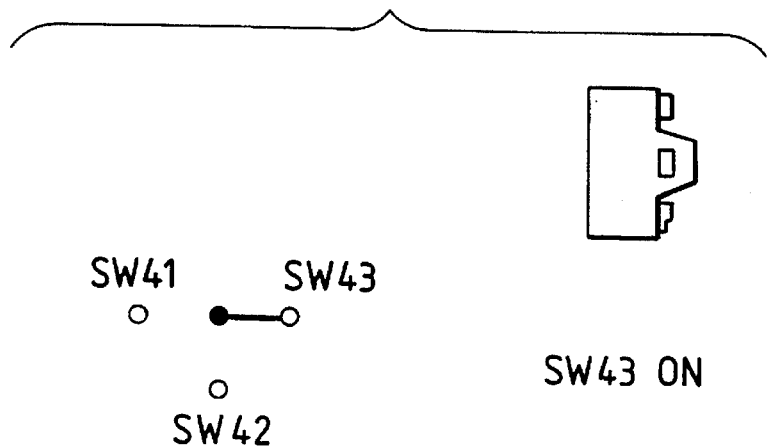

FIGS. 4A, 4B and 4C show the relationship between the camera position and the attitude detecting unit 7 employing a pendulum.

When the camera is held in the horizontal attitude, a switch SW42 is turned on, whereby the horizontal camera attitude is recognized and the LED's 32 and 33 are selected among four LED's.

When the camera is in the vertical attitude, a switch SW41 or SW43 is turned on in said attitude detecting unit 7, whereby the LED's 31 and 32, or the LED's 33 and 34 are respectively selected.

Figure 5:
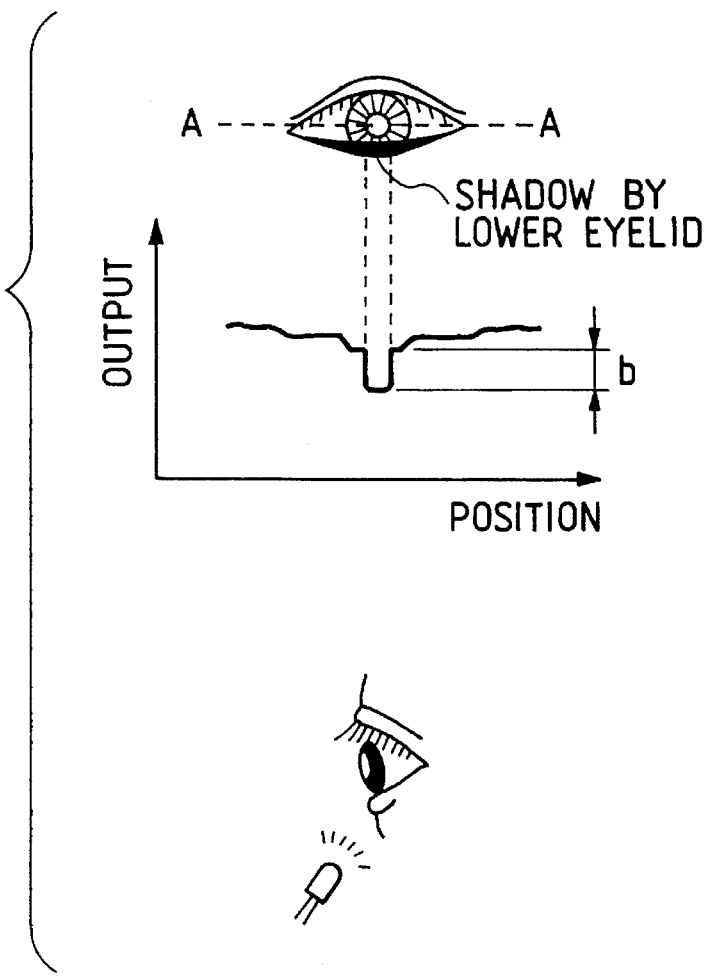
FIG. 5 is a view showing an example of the output of a photoelectric converting element 117.

Such selection provides an output of the eye illuminated by said LED's, as shown in FIG. 5. As explained above, the eye is illuminated from the side of the lower eyelid, whereby the shadow is less likely formed, and the difference b in the outputs of the pupil and the iris becomes larger than the difference a in the conventional configuration. Consequently the position of the pupil center can be more precisely calculated.

Figure 6:
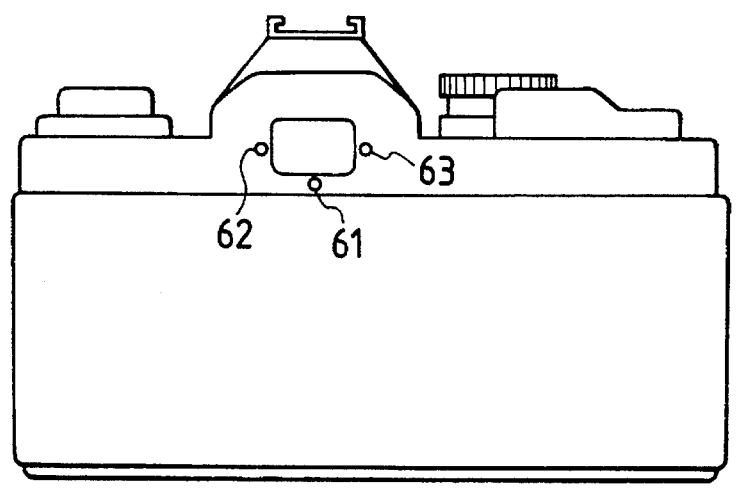
FIG. 6 is a view showing another arrangement of the light-sources in the second illumination unit 11.

FIG. 6 shows another embodiment of the arrangement of the light sources 120 in the second illumination unit for illuminating the eye, for detecting the position of the pupil center.

As shown in FIG. 6, the light sources 120 are composed of three LED's 61, 62, and 63 positioned respectively in the vicinity of the center of the lower, left and right sides of the eyepiece lens. Said three LED's are selectively used by the light source selecting unit 12, according to the output of the attitude detecting unit 7. In this embodiment an LED positioned lower in the direction of gravity is selected.

When the camera is held in the horizontal position as shown in FIGS. 4A to 4C, a switch SW42 is turned on, whereby the horizontal camera attitude is recognized, and an LED 61 is selected among three LED's.

When the camera is in the vertical attitude, a switch SW41 or SW43 is turned on in said position detecting unit 7, and the corresponding LED 62 or 63 is selected. Also in this case, the illumination is made from the side of the lower eyelid, whereby the shadow is less likely formed, and the difference b between the outputs of the pupil and the iris becomes larger than the difference a in the conventional configuration. Consequently the position of the pupil center can be calculated more precisely.

In the following there will be explained the function of the camera with the sight line detecting device of the first embodiment.

Figure 7:
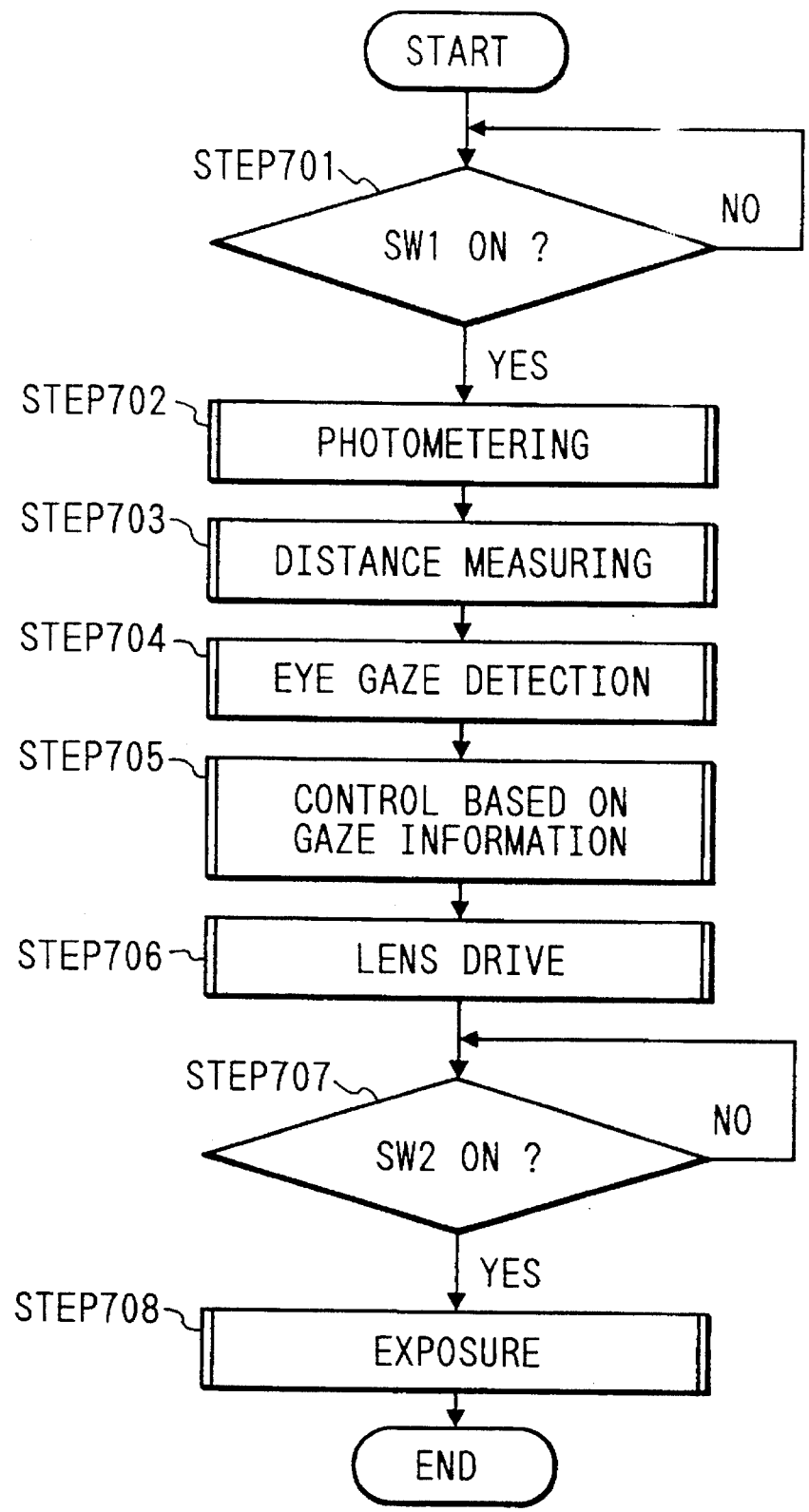
FIG. 7 is a flow chart showing a phototaking operation in the camera with the sight line detecting device of the first embodiment.

FIG. 7 is a flow chart showing the function of said camera with the sight line detecting device, in the phototaking operation from the turning-on of the power supply to the exposure (shutter release), and this flow is executed by the start of the power supply.

A step 701 discriminates whether the half-stroke switch SW1 is turned on, and, if on, the sequence proceeds to a step 702, but, if not, this step 701 is repeated.

A step 702 causes the photometry unit 3 to effect the light metering. As an example, the light metering is executed in each of plural areas defined in the phototaking field, and the measured values are stored in a memory in the control unit 1.

A step 703 causes the distance measuring unit 2 to effect distance measurement. As an example, the distance measurement is conducted in each of the distance measuring areas A1, A2, A3 defined in the finder 801 as shown in FIG. 8, and the measured values are stored in the memory in the control unit 1.

A step 704 executes the sight line detecting subroutine, for detecting the line of sight, from the positions of the Purkinje's first image and the pupil center, as will be explained later in more details.

A step 705 controls the light metering and the distance measurement, utilizing the information obtained in the steps 702 and 703 and based on the direction of the line of sight calculated in the step 704. As an example, the distance measurement is controlled according to the distance information of the distance measuring area A1 corresponding to the position of the line of sight indicated by a mark X (FIG. 8) and the light metering is controlled by the weighted average with the center of gravity at an area corresponding to the position of the line of sight indicated by a mark X.

A step 706 effects focusing by driving the phototaking lens 101, based on the distance information determined in the step 705.

A step 707 discriminates whether the full-stroke switch SW2 is turned on, and, if on, the sequence proceeds to a step 708, but, if not, this step 707 is repeated.

A step 708 causes the exposure unit 4 to execute the exposure operations including the mirror lifting, release of shutter curtains, mirror lowering, film advancement and shutter charging, based on the light metering information determined in the step 705. This routine is terminated by the completion of the exposure. However, after this step 708, the sequence may return to the step 701 and may continue this routine until the power supply is turned off.

In the following there will be explained the detection of the line of sight in the step 704.

Figure 9:
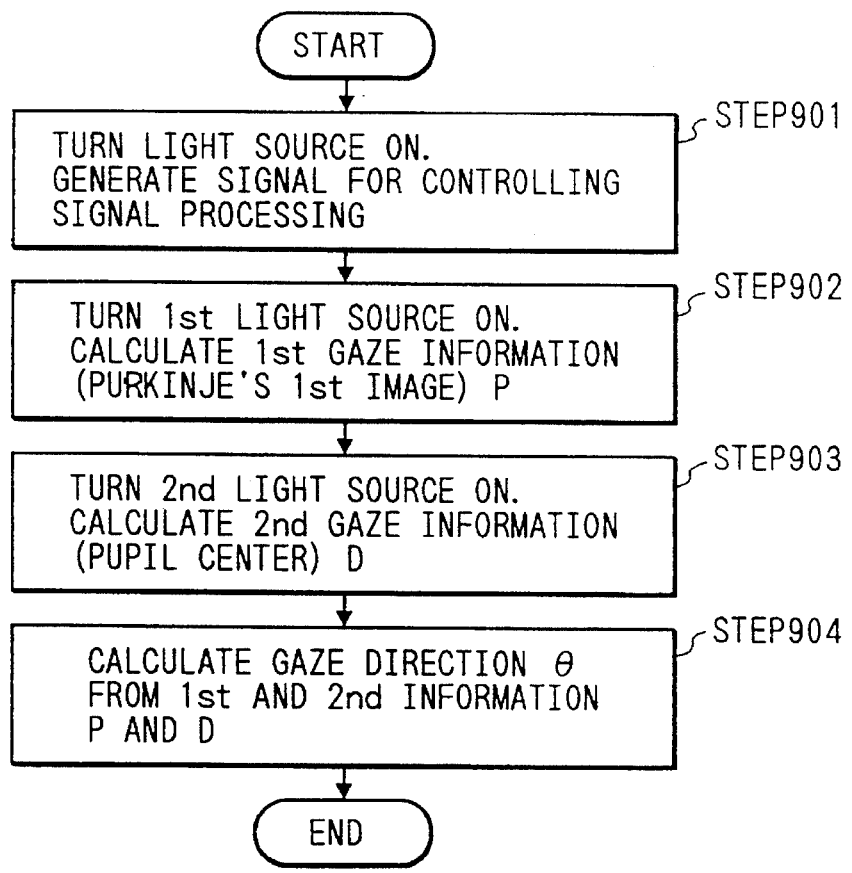
FIG. 9 is a flow chart of a sight line detecting subroutine in FIG. 7.

FIG. 9 is a flow chart of the sight line detecting subroutine.

Figure 10:
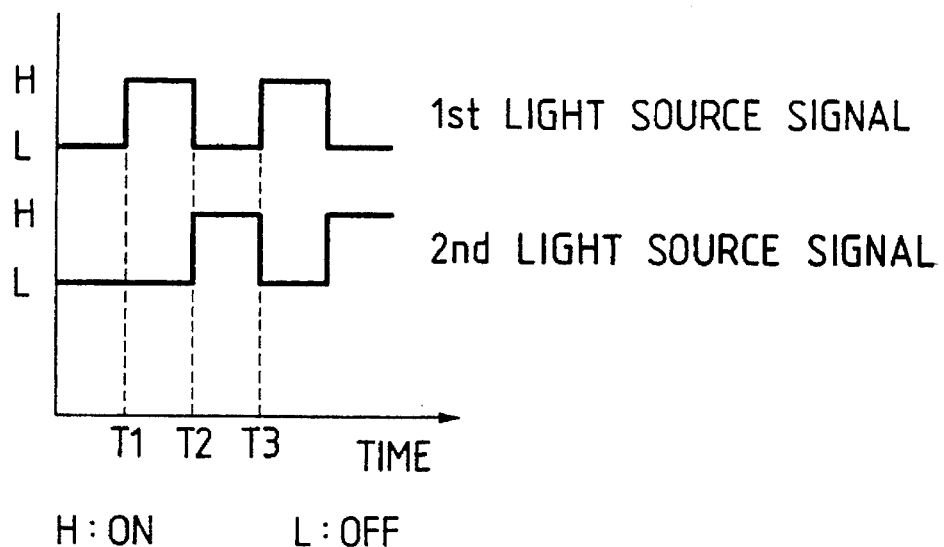
FIG. 10 is a timing chart showing the sight line detecting control by a CPU 1 in the flow shown in FIG. 9.
Figure 11:
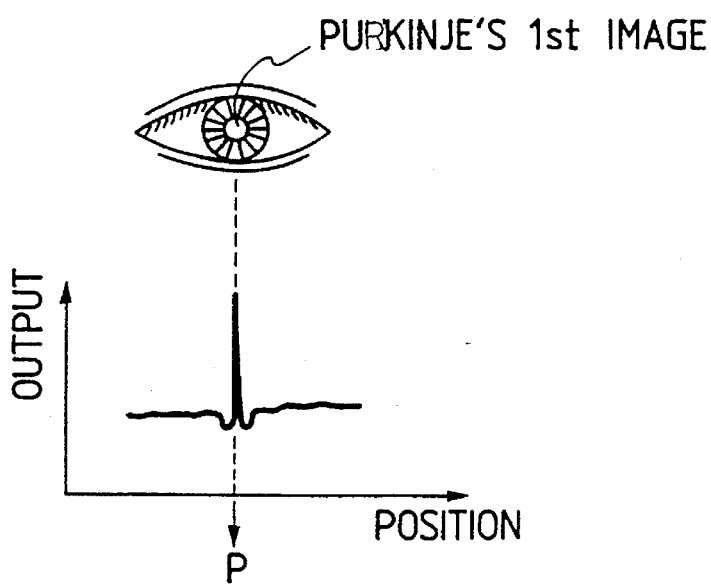
Figure 12:
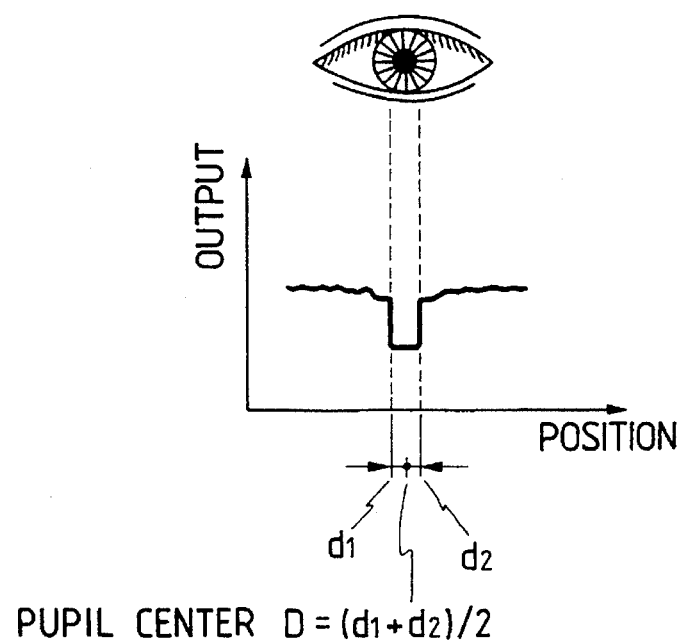

A step 901 generates signals for controlling the first and second illumination units 10, 11 (see FIG. 10) and a control signal for processing the signal from the light-receiving unit 6, thereby controlling the first and second illumination units 10, 11 and the signal processing for the detection of the line of sight. These operations are executed in the control unit 1. In FIG. 10, the abscissa indicates the elapsed time. At the upper side there is shown the control signal for controlling the first illumination unit 10 and for calculating the position of the Purkinje's first image, and, at the lower side, there is shown the control signal for controlling the second illumination unit 11 and for calculating the position of the pupil center. The lighting control of the first and second illumination units 10, 11 is not limited to the method explained above, and they may be turned on at the same time;

A step 902 effects the lighting control of the first illumination unit 10 and the processing of the signal from the light-receiving unit 6, based on the upper one, among the signals generated in the step 901. When the upper signal is in the high (H) level state, the light source of the first illumination unit 10 is turned on, and the position of the Purkinje's first image is calculated from the output signal of the light-receiving unit 6 in this state. Said position of the Purkinje's first image is determined as a peak position P in the output signal of the light-receiving unit 6, as shown in FIG. 11;

A step 903 effects the lighting control of the second illumination unit 11 and the processing of the signal from the light-receiving unit 6, based on the lower one among the signals generated in the step 901. When the lower signal is in the high (H) level state, the light source of the second illumination unit 11 is turned on, and the position of the pupil center is calculated from the output signal of the light-receiving unit 6 in this state. Said position is determined as the center D of boundaries d1, d2 of a recess in the output of the light-receiving unit 6, as shown in FIG. 12. The control signals of the upper and lower sides are correlated in time in the following manner. As shown in FIG. 10, both signals are in the low (L) level state until a time T1, so that the detection of the line of sight is not conducted. In a period from T1 to T2, the upper control signal is in the high level state while the lower control signal is in the low level state, so that the first illumination unit 10 is turned on to detect the position of the Purkinje's first image. The second illumination unit 11 is turned off, so that the detection of the position of the pupil center is not conducted. In a period from T2 to T3, the upper control signal is in the low level state while the lower control signal is in the high level state, so that the first illumination unit 10 is turned off and the detection of the Purkinje's first image is not conducted, while the second illumination unit 11 is turned on to detect the position of the pupil center. Thereafter the state of T1–T2 and that of T2–T3 are alternated, whereby the light sources are controlled by the light source switching unit 9, and the detection of the position of the Purkinje's first image and that of the position of the pupil center are alternately executed.

A step 904 calculates the direction θ of the line of sight, from the positional information P of the Purkinje's first image and the positional information D of the pupil center, determined in the steps 902 and 903. Said direction θ is calculated from the equation (1):

$$\theta = \sin^{-1}[(D-P)/(A-\rho)] \quad (1)$$

wherein A: distance from the center of rotation of eyeball to the center of pupil; and ρ: distance from the center of rotation of eyeball to the center of curvature of cornea.

Upon calculation of the direction θ of the line of sight according to the equation (1), the sight line detecting subroutine is terminated.

In the above-explained camera with the sight line detecting device, there are provided the first illumination unit 10 for detecting the Purkinje's first image and the second illumination unit 11 for detecting the pupil center, and the latter illuminates the eye of the photographer from the lower side (side of lower eyelid) regardless whether the camera is held in the horizontal or vertical attitude. Consequently there can be prevented the drawback in the conventional configuration that the eye-illuminating light source fop detecting the boundary between the pupil and the iris or between the black and white of the eye forms the shadow of the upper eyelid or eyelashes on the white, the black or the pupil of the eye, thus decreasing the difference a between the outputs corresponding to the pupil and the iris by the superposing of the shadow signal on said output signals. Thus the position of the pupil center can be calculated precisely.

Second Embodiment

Figure 13:
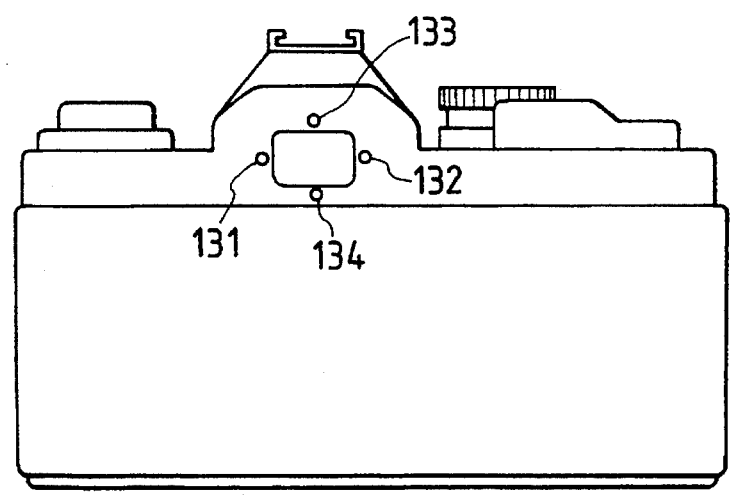
FIG. 13 is a view showing the arrangement of the light sources of the second illumination unit 11 to be employed in the camera with the sight line detecting device of a second embodiment of the present invention.

FIG. 13 illustrates a second embodiment of the present invention, wherein the light sources 120 of the second illumination unit 11 are composed of four LED's 131–134; positioned at the approximate centers of the left, right, upper and lower sides of the eyepiece lens. In other respects the second embodiment is substantially the same as the first embodiment. Said four LED's are selectively used by the light source selecting unit 12, according to the output of the attitude detecting unit 7, provided for detecting the camera position. In this second embodiment, there are selected two LED's which are horizontally positioned with respect to the direction of gravity, as will be explained in more detail with reference to FIGS. 4A to 4C.

When the camera is held in the horizontal position, the switch SW42 is turned on in the position detecting unit 7, whereby the LED's 131 and 132 are selected among four LED's.

Figure 14:
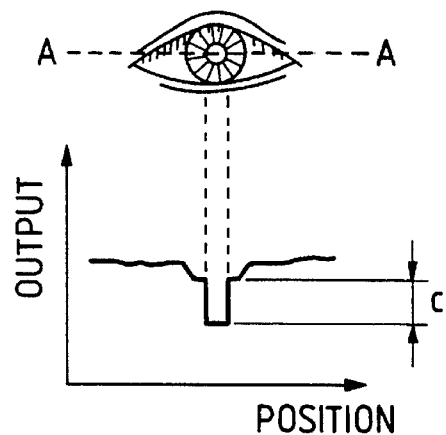
FIG. 14 is a view showing an example of the output of the photoelectric converting element 117 in the second embodiment.

When the camera is held in the vertical attitude, the switch SW41 or SW43 is turned on in said position detecting unit 7, whereby the LED's 133 and 134 are selected. Such LED selection effects the illumination of the eye from both sides thereof with scarce shadow formation, whereby the difference c between the outputs corresponding to the pupil and the iris is further enhanced as shown in FIG. 14 and the calculation of the pupil center can be easily and precisely conducted.

The above-explained camera with the sight line detecting device provides the effects substantially same as those in the first embodiment, and also provides the effect that the shadow is hardly formed in case the eye rotates or moves sideways. In the following there will be given a more detailed explanation on the processing of the signal from the light-receiving unit 6 in the sight line detecting subroutine in the first and second embodiments explained in relation to FIG. 9.

Figure 15A:
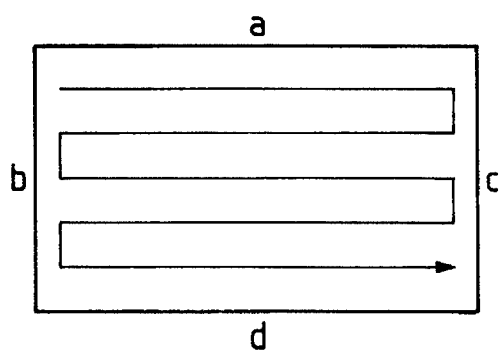
FIGS. 15A, 15B and 15C are views showing scanning directions of the photoelectric converting element 117 in the camera position shown in FIGS. 4A to 4C.
Figure 15B:
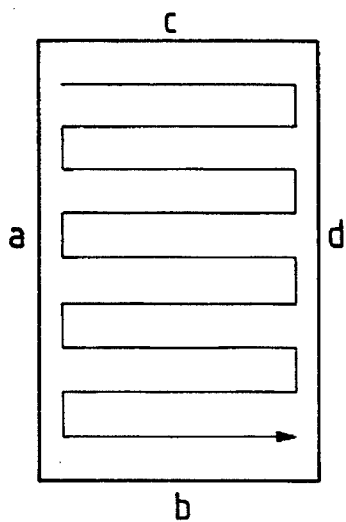
Figure 15C:
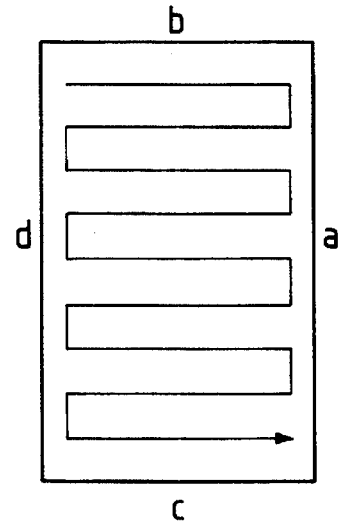

FIGS. 15A to 15C illustrate the scanning directions of the photoelectric converting element 117 in the light-receiving unit 6, in relation to the camera positions shown in FIGS. 4A to 4C.

The scanning direction of the element 117 shown in FIG. 15A corresponds to the camera position shown in FIG. 4A. As shown in FIG. 15A, the upper side of the photoelectric converting element 117 is called a, the lower side d, the left side b, and the right side c. In the camera position shown in FIG. 4A, where the switch SW42 is turned on, the element 117 is scanned in a direction from b to c, or from c to b, and this scanning operation is repeated from a to d (or in random order).

Also the scanning direction of the element 117 shown in FIG. 15B corresponds to the camera position shown in FIG. 4B. In such camera position shown in FIG. 4B, where the switch SW41 is turned on, the element 117 is scanned in a direction from a to d, or from d to a, and this scanning operation is repeated from c to b (or in random order).

Similarly the scanning direction of the element 117 shown in FIG. 15C corresponds to the camera position shown in FIG. 4C. In this camera position shown in FIG. 4C, where the switch SW43 is turned on, the element 117 is scanned in a direction from d to a, or from a to d, and this scanning operation is repeated from b to c (or in random order).

Figure 16A:
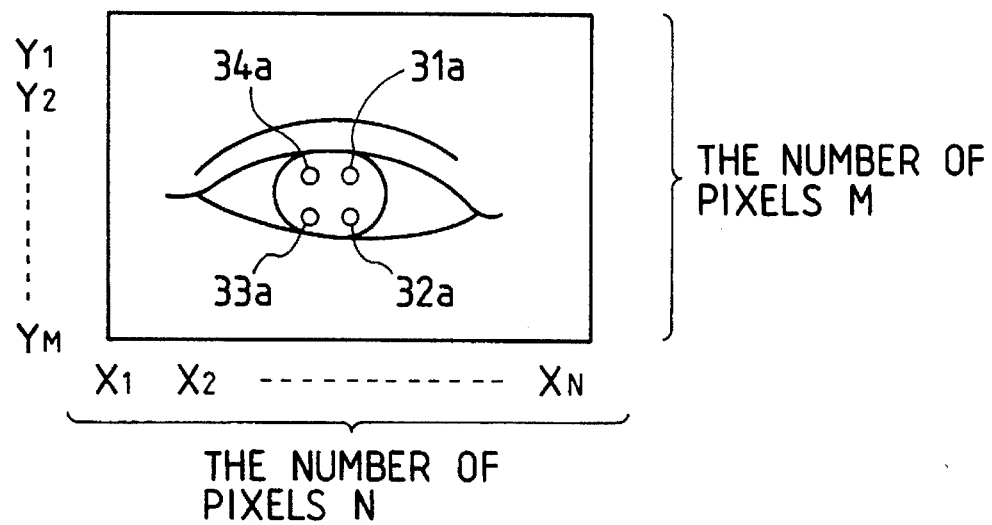
FIGS. 16A and 16B are views showing an image obtained from the photoelectric converting element 117 and arrays of elements therein.
Figure 16B:
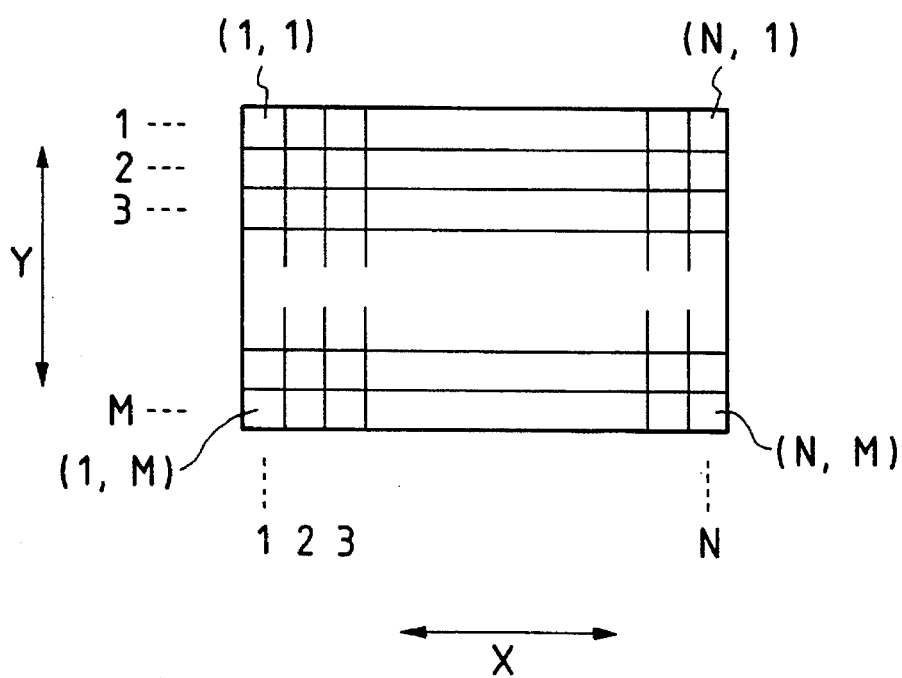

FIGS. 16A and 16B show the arrangement of pixels in the photoelectric converting element 117.

As shown in FIG. 16A, the element 117 has N and M pixels respectively in the lateral and vertical directions, and, in the laterally oblong position, the horizontal and vertical directions are defined as X- and Y-directions. Consequently the pixels are addressed as (X1, Y1) at the upper left corner, (XN, Y1) at the upper right corner, (X1, YM) at the lower left corner, and (XN, YM) at the lower right corner.

Figure 17:
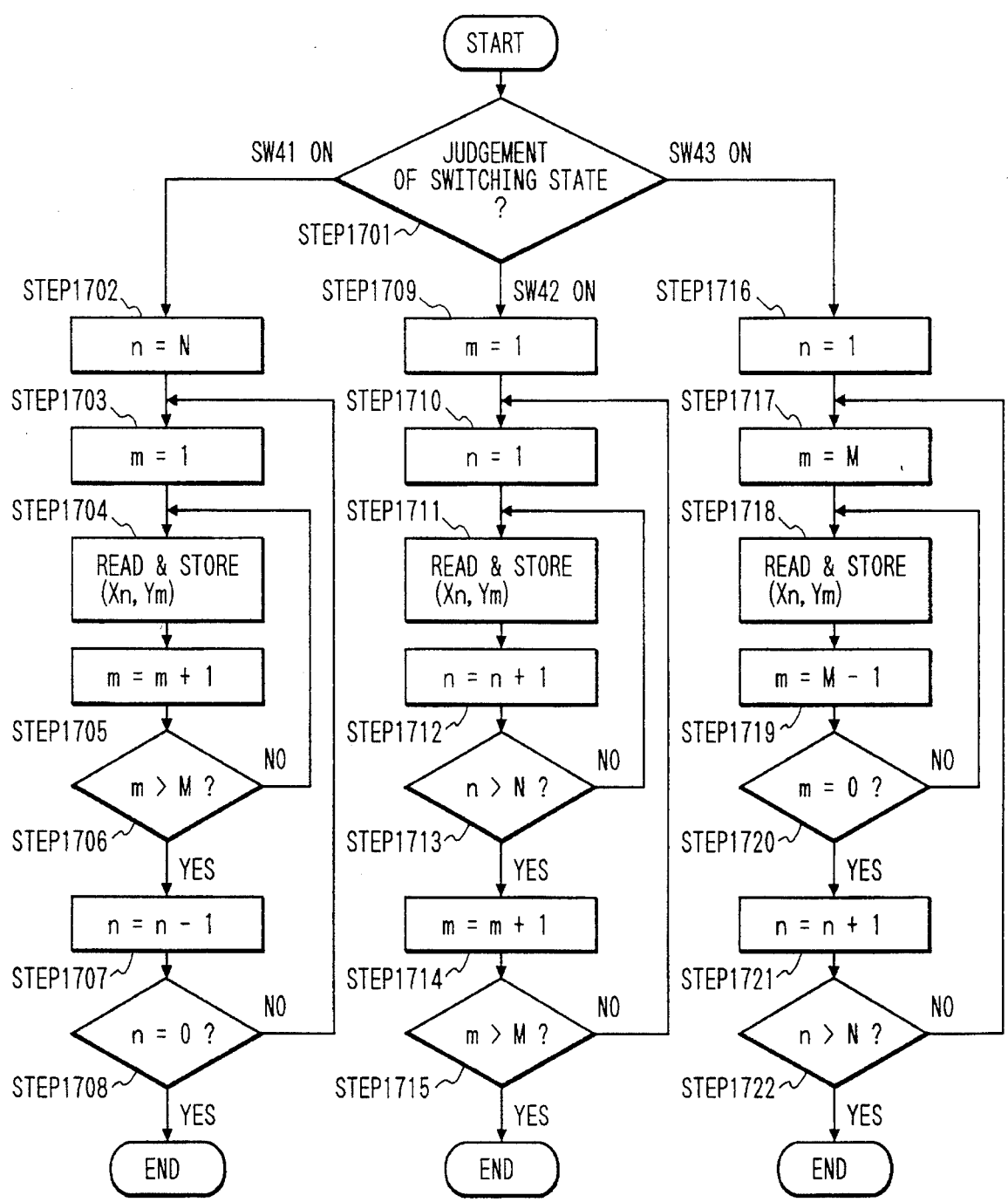
FIG. 17 is a flow chart showing the scanned processing of the photoelectric converting element 117 in the first and second embodiments.

FIG. 17 is a flow chart of the scanning process of the above-mentioned photoelectric converting element 117, and the scanning process will be explained in the following, with reference to FIG. 17:

A step 1701 discriminates the turned-on one of the switches SW41–SW43, and the sequence proceeds to a step 1702 if the switch SW41 is turned on, or a step 1709 if the switch SW42 is turned on, or a step 1716 if the switch SW43 is turned on.

A step 1702 designates N as the X-address n.

A step 1703 designates 1 as the Y-address m.

A step 1704 reads and stores the information of a pixel (XN, Y1) designated in the steps 1702 and 1703.

A step 1705 effects a step increment of the Y-address.

A step 1706 discriminates whether the increased Y-address m has exceeded M, and, if not, the sequence returns to the step 1704 thereby effecting the scanning operation in the horizontal direction, but, if exceeded, the sequence proceeds to a step 1707 for entering the scanning operation in a succeeding row.

A step 1707 effects a step decrement of the X-address n, thereby moving the address of the scanned row in the vertical direction of the image field.

A step 1708 discriminates whether the decreased X-address has reached 0. The sequence returns to the step 1704 until the X-address n reaches 0, thereby scanning all the horizontal rows in the image field.

In the above-explained steps 1702–1708, when the camera is in the position shown in FIG. 4B, the scanning operation of the element 117 is conducted, as shown in FIG. 15B, in the horizontal direction from the upper left corner of the image field to the lower right corner.

Also in steps 1709 to 1715 and in steps 1716 to 1722, the scanning operation is executed similarly from the upper left corner to the lower right corner, as respectively shown in FIGS. 15A and 15C.

The above-explained processes are based on the assumption that the scanning direction of the photoelectric converting element is variable. If said scanning direction cannot be changed, a similar process can be achieved by storing the output of the element 117 in a memory, and varying the order of readout of the stored data in the processing, according to the output of the position detecting unit. A similar process can also be achieved by interchanging the rows and columns of the output data of the element 117 in the processing, depending on the position of the camera.

Third Embodiment

In the foregoing first and second embodiments, the first sight line information P and the second sight line information D are respectively detected by the use of the first and second illumination units 10, 11, but both information P and D can be detected by the illumination with the second illumination unit 11 alone, without the first illumination unit 10.

Thus, as a third embodiment, there will be explained a camera with a sight line detecting device, capable of detecting the first and second sight line information P and D with the illumination by the second illumination unit 11 alone.

Figure 18:
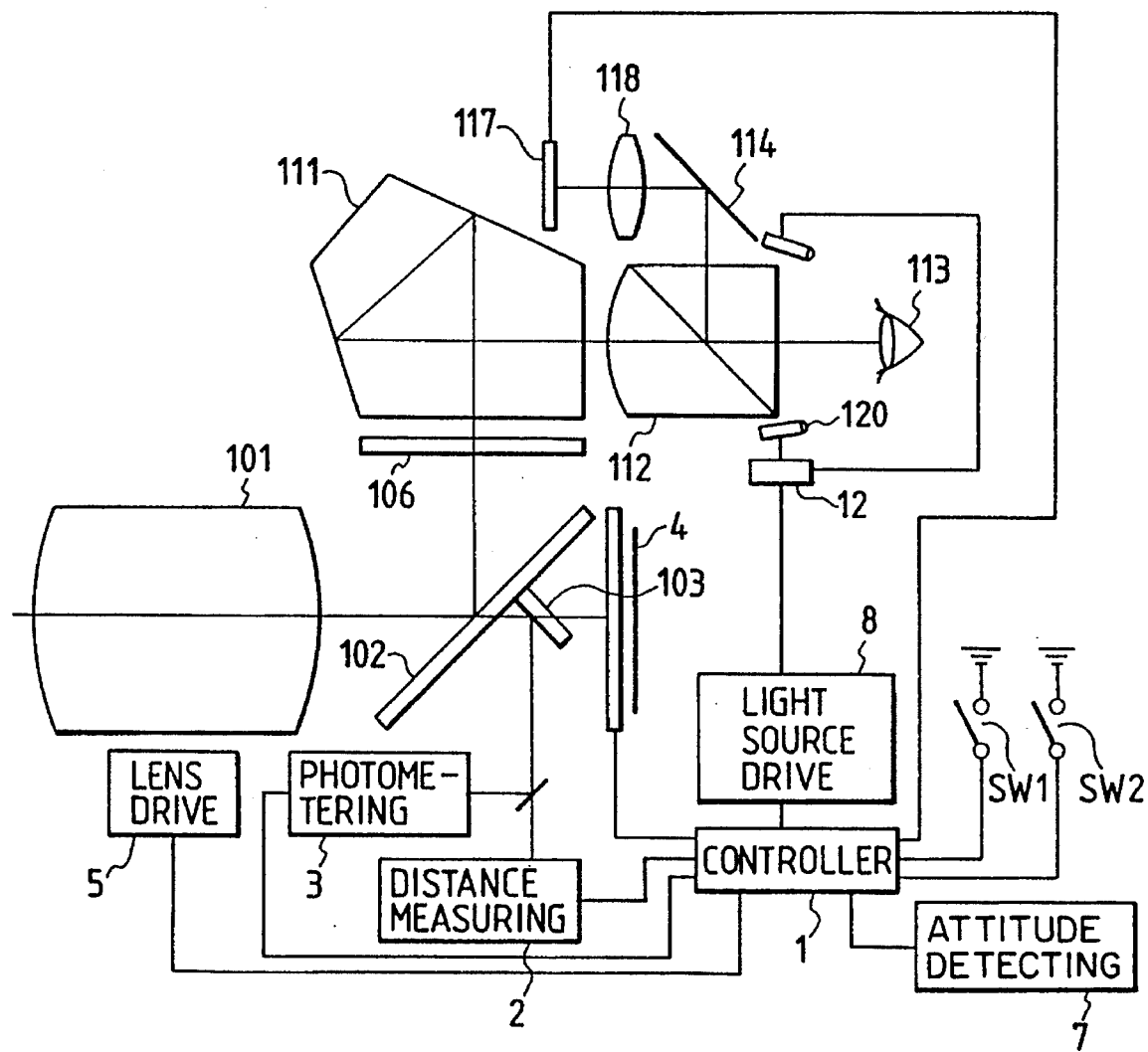
FIG. 18 is a schematic view of the camera with the sight line detecting device, constituting a third embodiment.

FIG. 18 shows the configuration of said third embodiment, including the optical system thereof. The configuration shown in FIG. 18 is same as that shown in FIG. 2, except that the first illumination unit 10 and the light source switching unit 9 are excluded, so that it will not be explained further.

In said third embodiment, the second illumination unit 11 serves to detect the Purkinje's first image and also to detect the position of the pupil center. The arrangement of the second illumination unit 11 can be same as shown in FIGS. 3, 6 and 13, for illuminating the eye of the photographer from the lower side (side of lower eyelid). Also the function of this third embodiment can be same as shown in the flow chart in FIG. 7.

FIG. 19 is a flow chart of the sight line detecting subroutine in the third embodiment, which will be explained in more details in the following:

A step 1901 generates a signal for the lighting control of the second illumination unit 11 and a control signal for processing the signal from the light-receiving unit 6, thereby controlling the second illumination unit 11 and the signal processing for sight line detection. These operations are executed in the control unit 1.

A step 1902 effects the lighting control of the second illumination unit 11 and the processing of the signal from the light-receiving unit 6, based on the signals generated in the step 1901, thereby calculating the position of the Purkinje's first image and of the pupil center.

Figure 21:
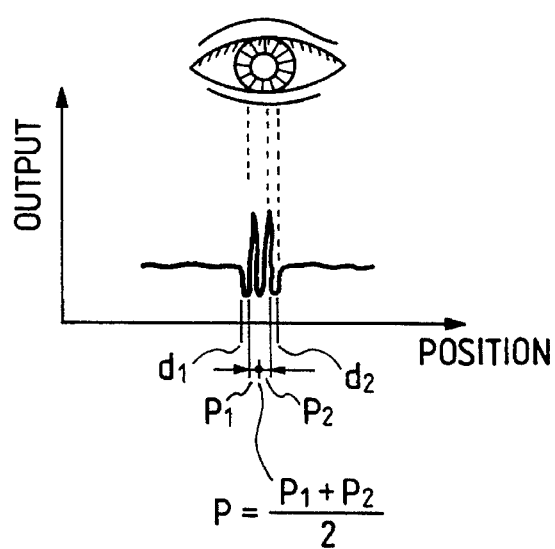
FIG. 21 is a view showing an example of the output of the photoelectric converting element 17 in the third embodiment.

In the light source arrangement shown in FIGS. 3 and 13, there are formed two Purkinje's first images by the light sources 120 as shown in FIG. 21, but the position of the Purkinje's first image can be determined, as disclosed in the Japanese Patent Laid-Open Application No. 2-264633, as the center P of the peak positions P1 and P2 in the output of the light-receiving unit 6, as shown in FIG. 21. Also in the light source arrangement shown in FIG. 6, said position can be determined as the peak position P of the output of the light-receiving unit 6, as shown in FIG. 11. Also the position of the center of the pupil can be determined as the center D of the boundaries d1, d2 of the recess in the output of the light-receiving unit 6;

A step 1903 calculates the direction θ of the line of sight, from the positional information P of the Purkinje's first image and the positional information D of the center of the pupil, determined in the step 1902. The calculation of said direction θ is executed according to the equation:

$$\theta = \sin^{-1}[(D-P)/(A-p)]$$

wherein

A: distance from the center of rotation of the eyeball to the center of the pupil; and ρ: distance from the center of rotation of the eyeball to the center of curvature of the cornea.

Upon calculation of the direction θ of the line of sight by the foregoing equation, the sight line detecting subroutine is terminated.

The processing of the signal from the photoelectric converting element 117 can be conducted in a similar manner as in the first and second embodiments, as shown in FIG. 17. However, the scanning method of the element 117 will be explained in the following with reference to FIGS. 20A to 20C, as it is different from that in the first or second embodiment.

Like FIGS. 15A to 15C, FIGS. 20A to 20C show the scanning directions of the photoelectric converting element 117 in the light-receiving unit 6, corresponding to the camera positions shown in FIGS. 4A to 4C.

Figure 20A:
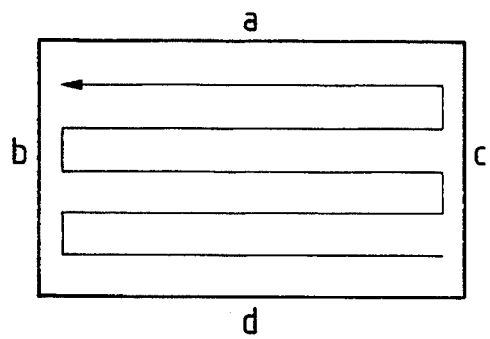
FIGS. 20A, 20B and 20C are views showing the scanning directions of the photoelectric converting element in a camera position shown in FIGS. 4A to 4C.

The scanning direction of the element 117 shown in FIG. 20A corresponds to the camera position shown in FIG. 4A. As in FIG. 15A, the upper side of the element 117 is named as a, the lower side as d, the left side as b, and the right side as c. In the camera position shown in FIG. 4A, where the switch SW42 is turned on, the photoelectric converting element 117 is scanned in a direction from b to c, or from c to b, and this scanning operation is repeated from d to a.

Figure 20B:
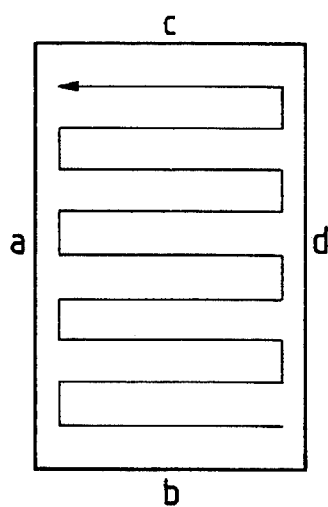

The scanning direction of the element 117 shown in FIG. 20B corresponds to the camera position shown in FIG. 4B. In this camera position, where the switch SW41 is turned on, the scanning operation of the element 117 is conducted in a direction from a to d, or from d to a, and this scanning operation is repeated from b to c.

Figure 20C:
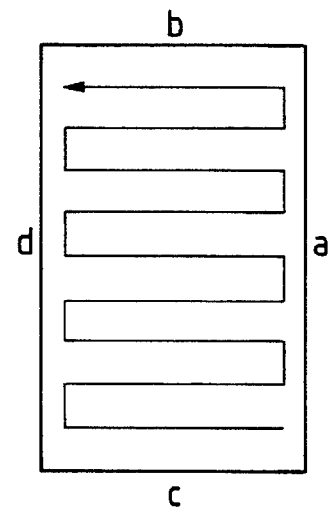

Similarly, the scanning direction of the element 117 shown in FIG. 20C corresponds to the camera position shown in FIG. 4C. In this camera position, where the switch SW43 is turned on, the scanning operation of the element 117 is conducted in a direction from d to a, or from a to d, and this scanning operation is repeated from c to b.

In this third embodiment, as shown in FIGS. 20A, to 20C, the photoelectric converting element is scanned from the lower end to the upper end, in the direction of gravity, in the image field. Since the eye of the photographer is illuminated from the lower side (side of the lower eyelid), the Purkinje's first image is generated in the lower part of the image field, so that the scanning operation of the photoelectric converting element 117 from the lower end enables faster detection of the Purkinje's first image, and the effect of illumination of the eye of the photographer from the lower side can be fully exploited.

In the camera with the sight line detecting device of the above-explained third embodiment, the second illumination unit 11 is provided for detecting the Purkine's first image and the pupil center and switches the light sources 120 according to the result of detection by the camera attitude detecting unit 7, so as to illuminate the eye of the photographer from the lower side (side of the lower eyelid), or from the horizontal direction. Consequently there can be avoided the drawback in the conventional configuration that the eye-illuminating light source for detecting the boundary of the pupil and the iris or of the black and white of the eye forms a shadow of the upper eyelid or eyelashes on the white, black or pupil of the eye, thereby reducing the difference a of the outputs corresponding to the pupil and the iris, due to the superposition of the shadow signal on the signal of eye image. Thus the position of the pupil center can be precisely calculated. Also there can obtained an advantage of dispensing with the separate illumination unit for detecting the Purkinje's first image, required in the camera of the first or second embodiment.

Fourth Embodiment

In contrast to the first to third embodiments in which the light sources are automatically switched according to the detection of the horizontal or vertical camera attitude, this fourth embodiment allows manual switching of the light sources by the photographer.

Figure 22:
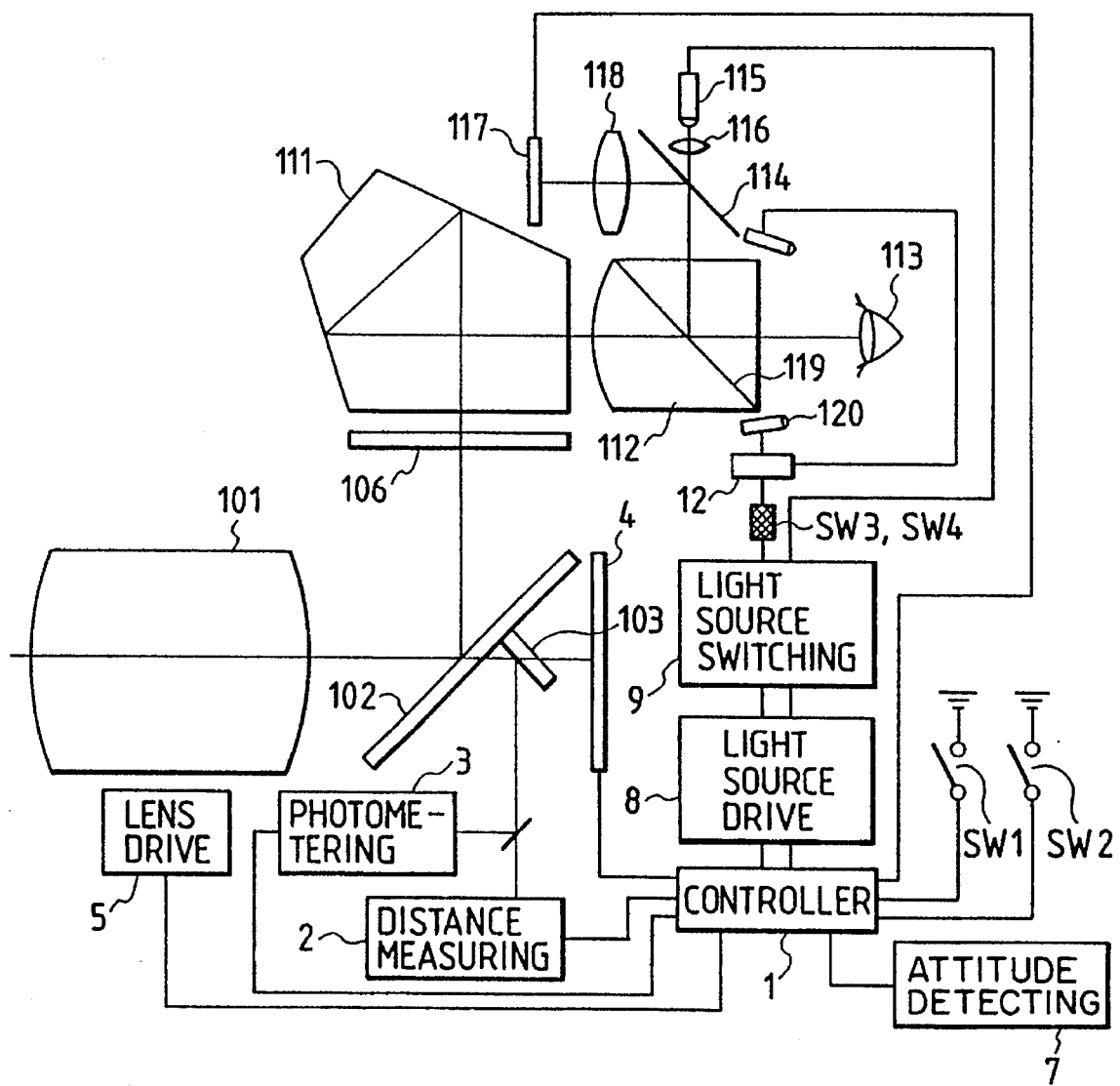
FIGS. 22 and 23 are schematic views of the camera with the sight line detecting device, constituting a fourth embodiment.
Figure 23:
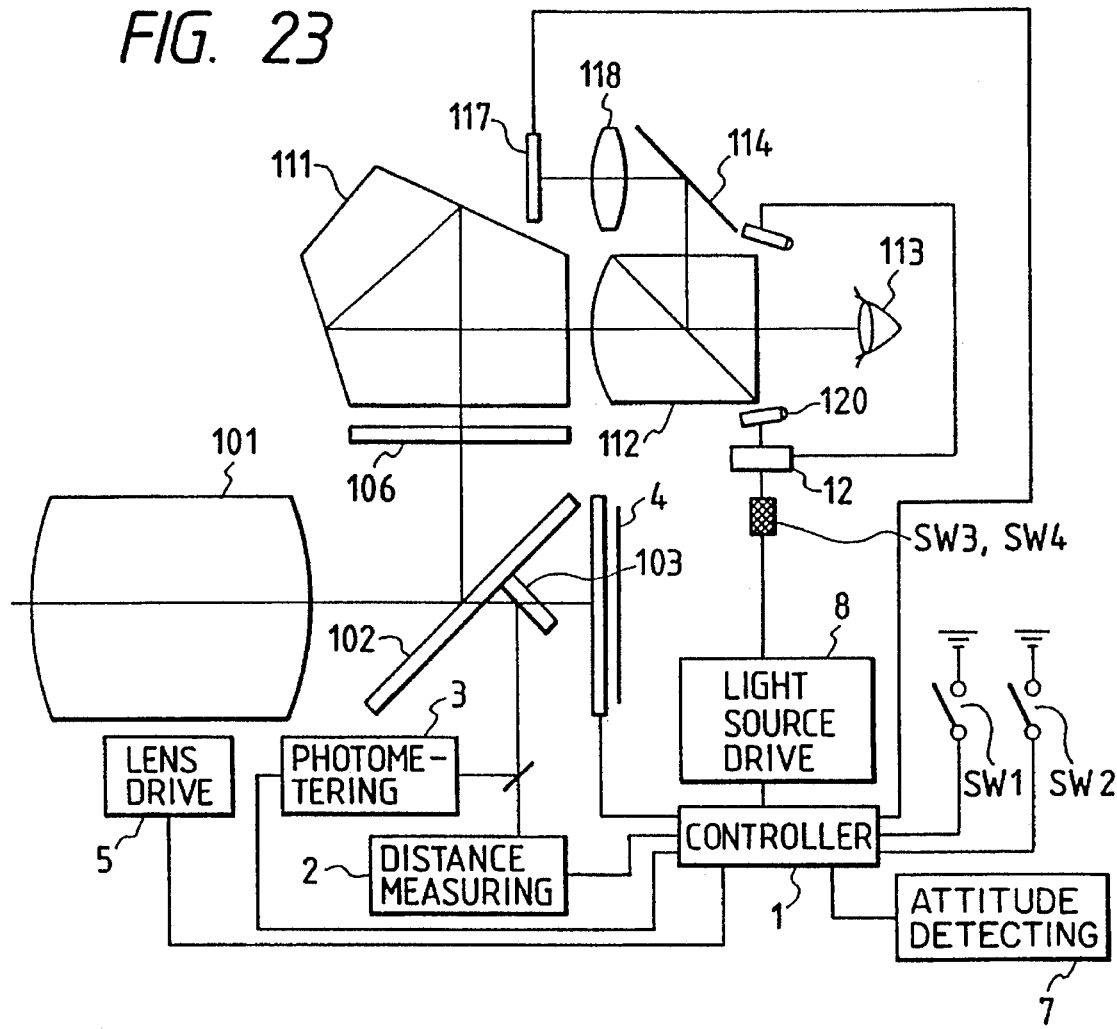

FIGS. 22 and 23 show configurations of a camera with a sight line detecting device of the fourth embodiment.

The configuration shown in FIG. 22 is identical with that of the first and second embodiments shown in FIG. 2, except for the addition of a light source switch mode selecting switch SW3 for selecting the automatic or manual switching of the light sources, and a light source selecting switch SW4 for manual switching of the light sources. Also the configuration shown in FIG. 23 is identical with that of the third embodiment shown in FIGS. 16A and 16B, except for the addition of the light source switch mode selecting switch SW3 and the light source selecting switch SW4.

Figure 24:
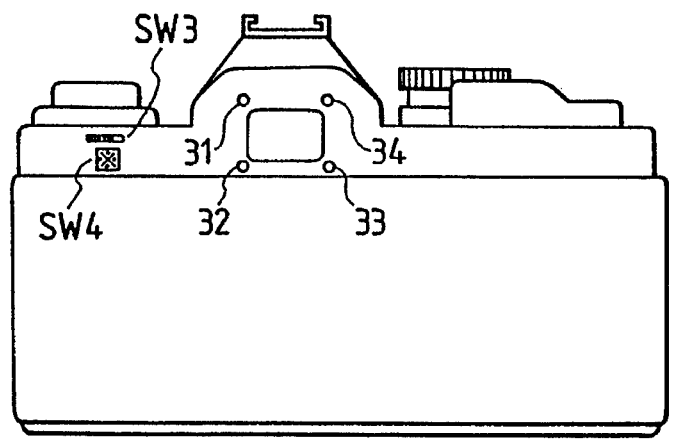
FIG. 24 is a view showing the arrangement of the second illumination unit 11 and the switches SW3, SW4 for use in the camera with the sight line detecting unit of the fourth embodiment.
Figure 25:
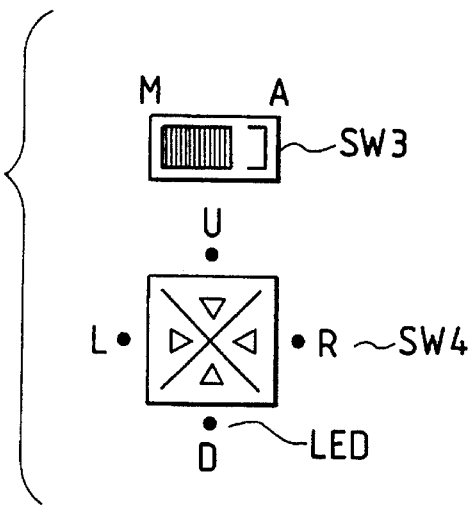
FIG. 25 is a magnified view of the switches SW3, SW4 shown in FIG. 24.

FIG. 24 shows an example of arrangement of said switches SW3, SW4. As shown in FIG. 24, said switches are provided in the upper left portion, in the rear side, of the camera. FIG. 25 is a magnified view of the switches SW3, SW4 shown in FIG. 24. The switch SW3 is moved to a side M, as shown in FIG. 25, in case of manual switching of the light sources, but is moved to a side A in case of automatic light source selection according to the detection of the camera attitude. Also LED's are provided adjacent to characters L, R, U, D indicating the directions of the switch SW4, and said LED's will be explained later.

In the following there will be explained the method of light source selection, in case the switch SW3 is positioned at the side M. In this embodiment four selections can be made with a single switch, as will be explained in the following with reference to FIG. 24. As an example, the light sources 31, 34 can be selected by depressing the upper part, marked U, of the switch SW4.

Figure 26:
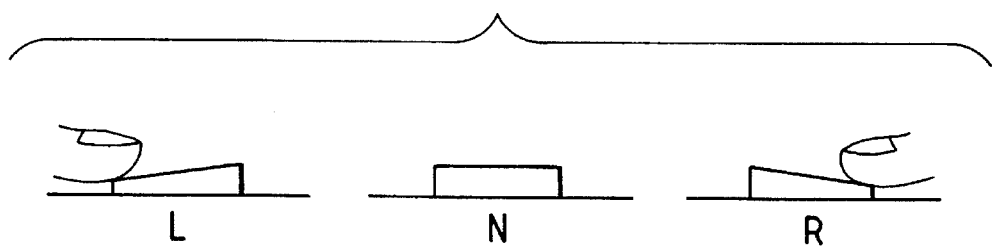
FIG. 26 is a view showing the method of selecting the switch SW4.

FIG. 26 shows the switch operations in case of selecting the light sources 31, 32, or 33, 34 shown in FIG. 24. A view N indicates a free state of the switch SW4. For selecting the L side, the left-hand half of the switch SW4 is depressed (as indicated by a view L) whereby the light sources 31, 32 at the left side are selected, and the switch returns to the state N when the finger is lifted. For selecting the R side, the right-hand half of the switch SW4 is depressed (as indicated by a view R) whereby the light sources 33, 34 are selected, and the switch returns to the state N when the finger is lifted. The side U or D can be selected in a similar manner.

Figure 27:
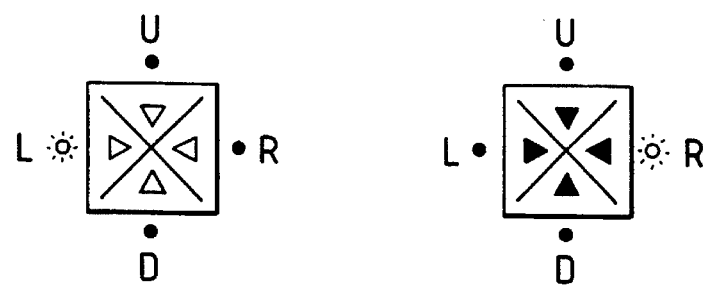
FIG. 27 is a view showing the display method, allowing the photographer to confirm the light source selected by the switch SW4.

FIG. 27 shows the functions of the LED's provided adjacent to the switch SW4.

These LED's are provided for confirming the direction of the selected light sources, and an LED in the selected direction is turned on. For example, if the side L is selected as shown in FIG. 26, the LED at the L side is turned on. Similarly, if the side R, U or D is selected, a corresponding LED is turned on.

Figure 28:
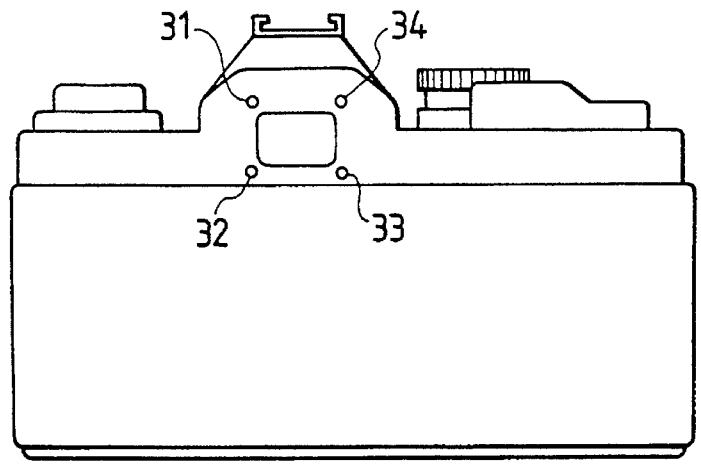
FIGS. 28 to 30 are views showing combinations of the light sources selectable by the switch SW4.
Figure 29:
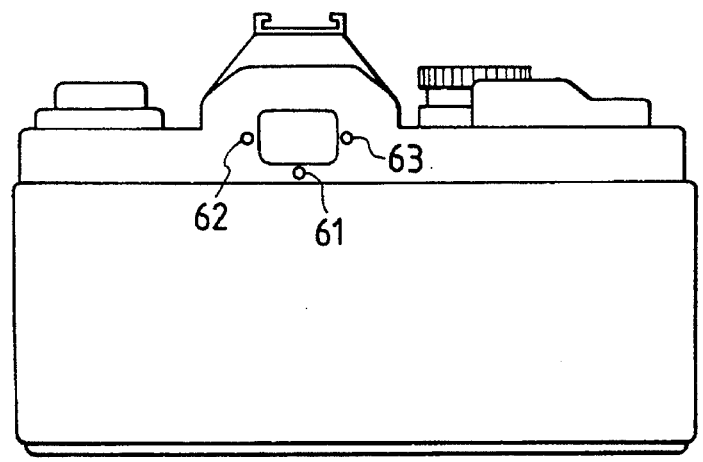
Figure 30:
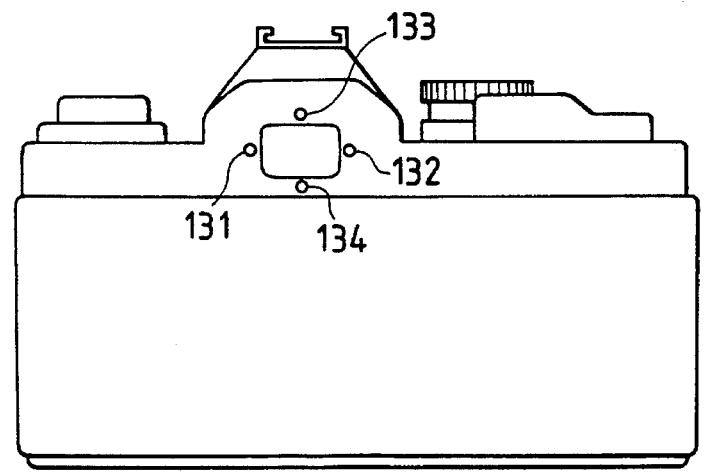

FIGS. 28 to 30 show the relationship between the light source combination in the manual selection and the switch SW4, in the light source arrangement shown in the first to third embodiments. In FIG. 28, four light sources 31–34 are provided respectively at the corners of the view finder, and the light sources 32, 33 are selected in response to the selection of D in the switch SW4; 31, 34 in response to the selection of U; 31, 32 in response to the selection L; or 33, 34 in response to the selection of R. In FIG. 29, the light sources are provided at the centers of the left, right and lower sides of the view finder, and the light source 61, 62 or 63 is selected respectively in response to the selection of D, L or R by the switch SW4. In this arrangement there is no light source corresponding to U, and, if the side U is depressed, the previously selected light source continues to be selected. In FIG. 30, light sources are provided at the approximate center of the sides of the view finder, and the light sources 131, 132 are selected in case U or D is depressed, while those 133, 134 are selected in case L or R is depressed.

The processes other than the light source selection will not be explained as they are same as those in the foregoing first to third embodiments.

Fifth Embodiment

The fifth embodiment is to turn on all the light sources provided on the camera, and to detect, at the processing, the image formed by the light source positioned below the eye.

FIG. 16A shows an example of the image obtained by the photoelectric converting element 117, when all the light sources are turned on in the arrangement shown in FIG. 25. Light points 31a, 32a, 33a, 34a are corneal reflected images of the lights emitted from the light sources 31, 32, 33, 34.

In the processing of such image data, the camera attitude is detected from the output of the attitude detecting unit 7, and the scanning operation of the photoelectric converting element 117 is, for example, conducted from the lower side as shown in FIGS. 20A to 20C or in a direction suitably designated by an unrepresented setting unit for the scanning direction, in such a manner that the reflected images formed by the light sources illuminating the eye of the photographer from the lower side (light points 32a and 33a in case of FIG. 16A) are detected at first.

Figure 31:
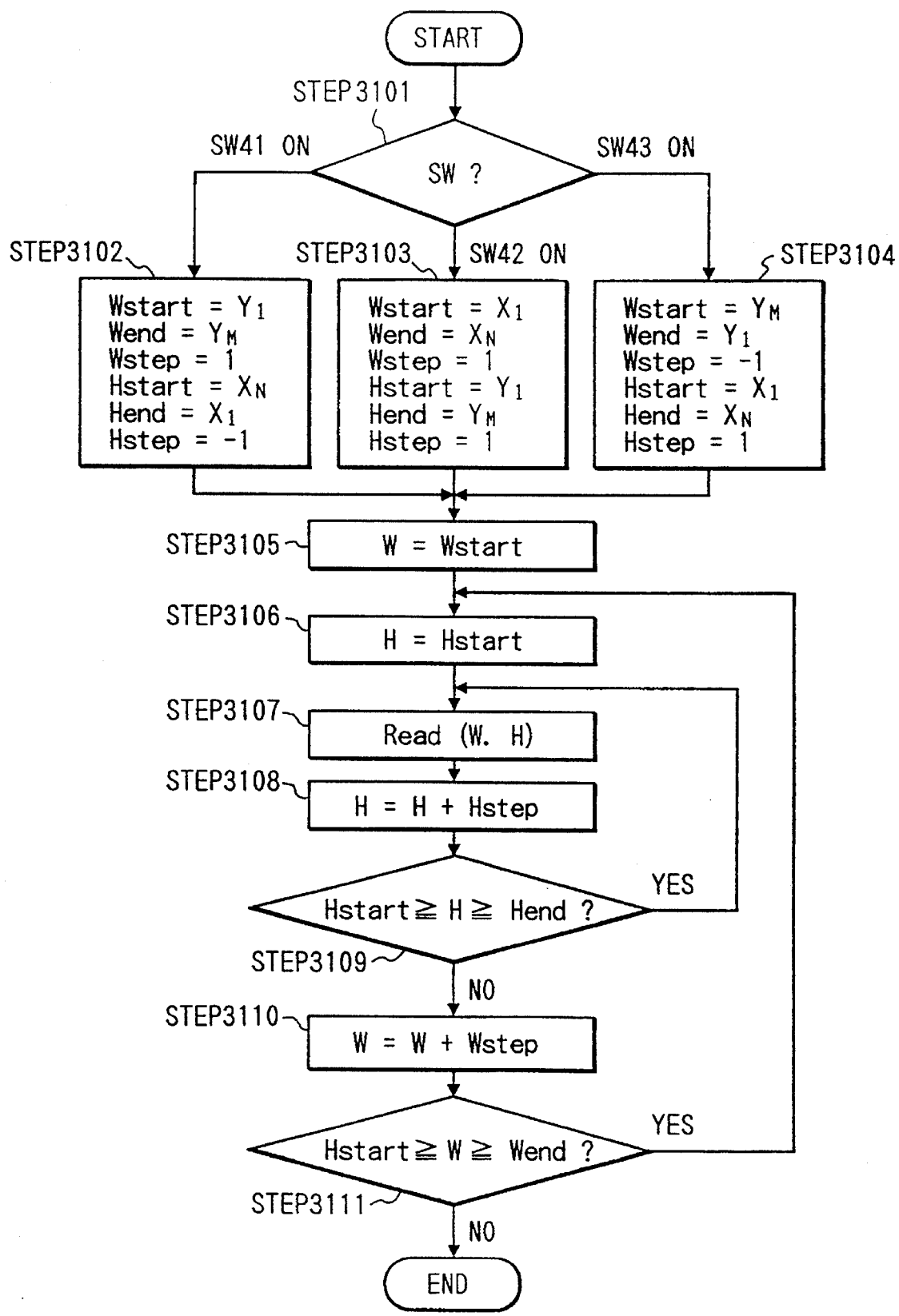
FIG. 31 is a flow chart showing the scan process of the photoelectric converting element 117 in a fifth embodiment.

FIG. 31 is a flow chart of an example of such processing in case the photoelectric converting element 117 is in the horizontally oblong position as shown in FIG. 16A, with M and N pixels respectively in the vertical and horizontal directions.

A step 3101 discriminates the turned-on one of the switches SW41–SW43, and the sequence proceeds to a step 3102, 3103 or 3104 respectively if the switch SW41, SW42 or SW43 is turned on.

Steps 3102–3104 set a horizontal start address Wstart, an end address Wend, a horizontal step Wstep, a vertical start address Hstart, an end address Hend and a vertical step Hstep, for the scanning of the element 117 in each state.

A step 3105 designates the horizontal address W of a first pixel to be read.

A step 3106 designates the vertical address H of the first pixel to be read.

A step 3107 reads the information of the designated pixel (W, H);

A step 3108 increases the horizontal address by Hstep;

A step 3109 discriminates whether the increased address H is positioned between the start address Hstart and the end address Hend, and, if positioned therebetween, the sequence returns to the step 3107 to continue the data reading, but, if not, the sequence proceeds to a step 3110.

A step 3110 increases the horizontal address by Wstep.

A step 3111 discriminates whether the increased address is positioned between the start address Wstart and the end address Wend, and, if positioned therebetween, the sequence returns to the step 3106 to continue the data reading, but, if not, the present flow is terminated.

In the foregoing all the pixels of the photoelectric converting element 117 are scanned, but the scanning area, scanning direction and the scanning start point can be arbitrarily selected by the corresponding settings of the horizontal start address Wstart, end address Wend, horizontal step Wstep, vertical start address Hstart, end address Hend and vertical step Hstep.

In the foregoing explanation, the scanning operation is conducted in the horizontal direction, but it may also be conducted in the vertical direction. Certain photoelectric converting elements allow the scanning operation only in a predetermined direction and in a predetermined pixel position, but, in such case, there may be adopted the aforementioned method of storing the output of the element in a memory and suitably varying the order of data readout from said memory at the data processing.

As explained in the foregoing, in the present invention, the second illumination unit 11 for determining the position of the pupil center is so constructed as to illuminate the eye from the lower side with respect to the direction of gravity, whereby the shadow of the upper eyelid or eyelashes is less likely formed and the position of the pupil center can therefore be detected more precisely.

Also a suitable setting of the output start point of the photoelectric converting element 117, receiving the eye image of the photographer, achieves faster processing of the sight line detection.

What is claimed is:
1. A sight line detecting device, comprising:
a first illumination device having a light source disposed to illuminate an eye of a user for detection of a corneal reflected image of the eye;
a second illumination device having a plurality of light sources disposed to illuminate the eye for detection of a boundary between the pupil and the iris or between the white and the black of the eye;
an attitude detecting section which detects an attitude of the sight line detecting device;
a selecting section which selects one or more light sources to be activated among said light sources of said second illumination device based on an output from said attitude detecting section;
a light receiving section disposed to receive light from the light sources of said first and second illumination devices reflected by the eye; and
a sight line analyzing device which determines a sight line of the user based on an output from said light receiving section.

2. A sight line detecting device according to claim 1, wherein said selecting section selects at least one light source among said plurality which is lower with respect to a direction of gravity than another light source of said plurality, based on the output from said attitude detecting section.

3. A camera with a sight line detecting device, said sight line detecting device comprising:
a first illumination device having a light source disposed to illuminate an eye of a photographer for detection of a corneal reflected image of the eye;
a second illumination device having a plurality of light sources disposed to illuminate the eye for detection of a boundary between the pupil and the iris or between the white and the black of the eye;

an attitude detecting section which detects an attitude of the camera;

a selecting section which selects one or more light sources to be activated among said light sources of said second illumination device based on an output from said attitude detecting section;

a light receiving section disposed to receive light from the light sources of said first and second illumination devices reflected by the eye; and a sight line analyzing device which determines a sight line of the photographer based on an output from said light receiving section.

4. A camera according to claim 3, including a finder and wherein said plurality of light sources of said second illumination device is disposed around said finder.

5. A camera according to claim 4, wherein said plurality of light sources includes four light sources arranged such that a first pair thereof is substantially horizontally aligned when said camera is in a horizontal attitude and a second pair thereof is substantially horizontally aligned when the camera is in a vertical attitude, and said selecting section selects said first pair when said output of said attitude detecting section indicates a horizontal attitude and selects said second pair when said output of said attitude detecting section indicates a vertical attitude.

6. A camera according to claim 4, wherein said plurality of light sources includes four light sources arranged such that, when said camera is in a horizontal attitude, a first pair thereof is substantially horizontally aligned and a second pair thereof is substantially horizontally aligned, and such that, when said camera is in a vertical attitude, a third pair thereof is substantially horizontally aligned and a fourth pair thereof is substantially horizontally aligned, and wherein said selecting section selects a lower of said first and second pairs with respect to a direction of gravity when said output of said attitude detecting section indicates a horizontal attitude and selects a lower of said third and fourth pairs with respect to the direction of gravity when said output of said attitude detecting section indicates a vertical attitude.

7. A sight line detecting device, comprising:

an illumination device having a plurality of light sources for illuminating an eye of a user in order to determine a sight line;

a selecting section which selects one or more light sources to be activated among said plurality of light sources;

a sensor which receives light rays reflected by the eye;

an analyzing section which determines a sight line based on an output of said sensor; and an indicating device which indicates the one or more light sources selected by said selecting section.

8. A sight line detecting device according to claim 7, further comprising an attitude detecting section which detects an attitude of the sight line detecting device, and wherein said selecting section selects among said plurality of light sources according to an output of said attitude detecting section.

9. A sight line detecting device according to claim 7, further comprising a manually operable selection switch, and wherein said selecting section selects among said plurality of light sources in accordance with a state of said switch.

10. A sight line detecting device, comprising:

an image sensor having a two-dimensional arrangement of photosensor elements for receiving an image of an eye of a user;

an attitude detecting section which detects an attitude of said image sensor;

a sight line analyzing section which determines a lower portion of an image field of said image sensor with respect to a direction of gravity based on an output of said attitude detecting section, and which processes output information of said photosensor elements starting with the output information of a photosensor element in said lower portion of said image field to determine a sight line of the user.

11. A sight line detecting device according to claim 10, wherein a scanning order of said photosensor elements is variable and said sight line analyzing section varies the scanning order in accordance with the output of said attitude detecting section.

12. A sight line detecting device according to claim 10, further comprising a memory, and wherein output information of said photosensor elements is stored in said memory, and said sight line analyzing section processes the information from said memory starting with the output information of a photosensor element in said lower portion of the image field.

13. A sight line detecting device according to claim 10, further comprising a plurality of light sources which are turned on simultaneously to illuminate the eye of the user, and wherein said sight line analyzing section determines the sight line of the user based on outputs from said image sensor corresponding to a lower one or more of said plurality of light sources.

14. A sight line detecting device, comprising:

a light receiving section having plural photosensor elements for receiving an image of an eye of a user;

a sight line analyzing section which processes output information of said photosensor elements to determine a sight line of the user; and a designating section which can changeably designate which photosensor element output information is to be processed first and which photosensor element output information is to be processed last in a processing operation of said sight line analyzing section.

15. A sight line detecting device according to claim 14, further comprising a memory, and wherein output information of said photosensor elements is stored in said memory, and said sight line analyzing section processes the information from said memory beginning with the output information designated to be read first and ending with the output information designated to be read last.

16. A camera with a sight line detecting device, said sight line detecting device comprising:

an illumination section having a plurality of light sources disposed around a finder to illuminate an eye of a photographer;

a selecting section which selects one or more light sources to be activated among said plurality of light sources;

a sensor which receives light rays reflected by the eye;

an analyzing section which determines a sight line based on an output of said sensor; and an attitude detecting section having a switching device to detect whether the camera is in a horizontal attitude, a first vertical attitude, or a second vertical attitude;

wherein said selecting section activates a lower one of said light sources with respect to a direction of gravity in the detected attitude of the camera.

17. A camera with a sight line detecting device, said sight line detecting device comprising:

an illumination device having a plurality of light sources disposed around a finder for illuminating an eye of a user in order to determine a sight line;

a selecting section which selects one or more light sources to be activated among said plurality of light sources; and a sensor which receives light rays reflected by the eye;

an analyzing section which determines a sight line based on an output of said sensor; and an indicating device which indicates the one or more light sources selected by said selecting section.

* * * * *